US012048628B2

(12) United States Patent
Jongpaiboonkit

(10) Patent No.: US 12,048,628 B2
(45) Date of Patent: Jul. 30, 2024

(54) SYSTEMS AND METHODS OF COATING BONE MATERIAL

(71) Applicant: Warsaw Orthopedic, Inc., Warsaw, IN (US)

(72) Inventor: Leenaporn Jongpaiboonkit, Sterling, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/522,593

(22) Filed: Nov. 9, 2021

(65) Prior Publication Data
US 2023/0142212 A1 May 11, 2023

(51) Int. Cl.
*A61F 2/30* (2006.01)
*A61F 2/46* (2006.01)

(52) U.S. Cl.
CPC .. *A61F 2/3094* (2013.01); *A61F 2002/30971* (2013.01); *A61F 2002/4672* (2013.01); *A61F 2002/4674* (2013.01)

(58) Field of Classification Search
CPC ............................. A61F 2/3094; A61L 27/38
See application file for complete search history.

(56) References Cited

U.S. PATENT DOCUMENTS

| 5,556,379 | A | 9/1996 | Wolfinbarger |
| 5,591,398 | A | 1/1997 | Knaepler et al. |
| 8,663,672 | B2 * | 3/2014 | Manrique ............... A61L 27/38 |
| | | | 435/325 |
| 9,101,475 | B2 | 8/2015 | Wei et al. |
| 9,228,579 | B2 | 1/2016 | Stobbe |
| 9,554,920 | B2 | 1/2017 | Wei et al. |
| 9,744,043 | B2 | 8/2017 | Chen et al. |
| 10,119,108 | B2 | 11/2018 | Maggiore |
| 2002/0161449 | A1 | 10/2002 | Muschler |
| 2010/0075405 | A1 | 3/2010 | Broadley et al. |

FOREIGN PATENT DOCUMENTS

| WO | 2007048016 A2 | 4/2007 |
| WO | 2010142004 A2 | 12/2010 |

OTHER PUBLICATIONS

R1, Blood Rocker/Mixer, A-1 Medical Integration, 2019, pp. 1-12 (Year: 2019).*

(Continued)

*Primary Examiner* — Robert S Walters, Jr.
*Assistant Examiner* — Andrew J Bowman
(74) *Attorney, Agent, or Firm* — Sorell, Lenna & Schmidt, LLP

(57) ABSTRACT

A method of coating a bone material in a container is provided. The method comprising adding the bone material to an opening of the container and sealing the opening of the container so that the bone material is disposed within an interior of the container; adding a liquid coating material to the interior of the container through an inlet of the container so as to coat at least a portion of the bone material with the liquid coating material; removing any excess coating material from the container from the interior through an outlet of the container; and removing the coated bone material from the container. A system of coating bone material under a sterilized environment is also provided.

4 Claims, 9 Drawing Sheets

(56) References Cited

OTHER PUBLICATIONS

R2, Thomas Shaker, Thomas Scientific, 2018, pp. 1-10 (Year: 2018).*
International Searching Authority, European Patent Office, P.B. 5818, Patentlaan 2 NL-2280 HV Rijswijk International Search Report and the Written Opinion of the International Searching Authority International application No. PCT/US2022/045871, Date of mailing Jan. 23, 2023.

* cited by examiner

SYSTEMS AND METHODS OF COATING BONE MATERIAL

BACKGROUND

Bone defects or bone voids may be caused by several different factors including, but not limited to trauma, pathological disease, or surgical intervention. Because bone provides both stability and protection to an organism, these defects or voids can be problematic. To address these defects or voids, compositions that contain both natural and synthetic materials have been developed. These compositions may, depending upon the materials contained within them, be used to repair tissues and to impart desirable biological and/or mechanical properties.

Hybrid materials composed of organic polymers coated with inorganic minerals have attracted much attention in biology and medicine due to their combination of advantageous properties. Polymeric materials can be a desirable base material for biomedical applications, as they can be processed into a variety of sizes and geometries and can be designed to bioresorb or bioabsorb in a controllable timeframe. Therefore, polymeric biomaterials have been featured in a variety of applications, including medical devices, tissue engineering scaffolds, and drug delivery systems.

Also, calcium phosphate based mineral coatings represent desirable surfaces for biomedical applications, as they can be similar in composition to bone tissue and have been shown to promote favorable interactions with natural bone, a property termed "bioactivity". The surface modification technology associated with mineral coatings seeks to apply an apatite layer with an engineered nanoparticle sized morphology to the surface of a highly porous biphasic calcium phosphate surface. The mineral coated surface has been demonstrated to stimulate bone cells creating an enhanced cellular environment for bone healing. Currently, the applications of these materials are done by spraying, which is time consuming, expensive, requires large scale equipment, and difficult to ensure the proper distribution of the coating materials. This is particularly so when coating a large volume of bone material with a large volume of coating material. Also, as the surface technology accomplishes bone stimulation through nanoparticle sized morphology features, the application of nanoparticle sized coatings is still subjected to an end product sterilization.

While various materials are desirable and suitable for surface coating, particularly mineral coating on the bone materials, many coating materials cannot withstand harsh end product sterilization process. Another obstacle in applying these materials is the absence of an automated and/or systematic machine-assisted method for the coating application. Current coating methods require significant manipulation and direct contact with the bone materials in preparing and introducing the coating material to the bone materials. The materials are typically prepared and used under physiological solution. These materials require minimal processing and post-processing as they do not withstand harsh processing or sterilization. This obstacle further leads to inconsistency and difficulty in scaling up the coating process beyond a small batch prepared through standard test tubes and beakers. These obstacles sum up to a significant limitation in the choice of coating materials and the reaction conditions allowed for coating the bone materials.

Therefore, there is a need for coating the bone material without the end product sterilization including coating the bone material under a sterilized environment. It is beneficial to achieve a successful coating under an aseptic process. There is also a need for an efficient method for coating bone material, where the liquid coating to be applied can be closely monitored so that the integrity of the coating can be maintained throughout the coating process and the coating material can be easily removed and replenished. It is also beneficial to have a coating process completed in a sizable container capable being scaled up. It is also desirable to have a sterilized system that can complete the entire coating process with minimal direct contact and handling of the bone material.

SUMMARY

Systems and methods are provided for coating bone material, where the liquid coating to be applied to the bone material can be closely monitored so that the integrity of the coating can be maintained throughout the coating process and the coating material can be easily removed and replenished. There is also provided a coating process that can be completed in a container where the entire coating process can be completed within the container with minimal direct contact and handling of the bone material.

In one embodiment, a method of coating a bone material in a container is provided. The method comprises adding the bone material to an opening of the container and sealing the opening of the container so that the bone material is disposed within an interior of the container; adding a liquid coating material to the interior of the container through an inlet of the container so as to coat at least a portion of the bone material with the liquid coating material; removing any excess coating material from the interior of the container through an outlet of the container; and removing the coated bone material from the container.

In another embodiment, a method of coating a bone material in a container is provided. The method comprises adding the bone material to an opening of the container and sealing the opening of the container so that the bone material is disposed within an interior of the container; adding a liquid coating material to the interior of the container through an inlet of the container so as to coat at least a portion of the bone material with the liquid coating material; removing any excess coating material from the interior of the container through an outlet of the container; adding a second liquid coating material into the interior of the container through the inlet of the container to form a mineral coating on the bone material; removing any excess second coating material from the interior of the container through the outlet of the container; and removing the coated bone material from the container.

In some embodiments, a system for making a coated bone material under a sterilized environment is provided. The system comprises a container comprising an opening configured for adding bone material to be coated, a seal configure to enclose the bone material in the interior of the container, an inlet configured to add a coating liquid to the interior of the container, an outlet configured to remove any excess coating material from the interior of the container, and a sensor configured to sense a parameter within the interior of the container; a reactor configured to receive and hold the container, the reactor having a balance and a heating element; a bone material having the porosity to receive a coating; and a coating material.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits, and advantages of the embodiments will be apparent regarding the following description, appended claims and accompanying drawings.

Figure 1:
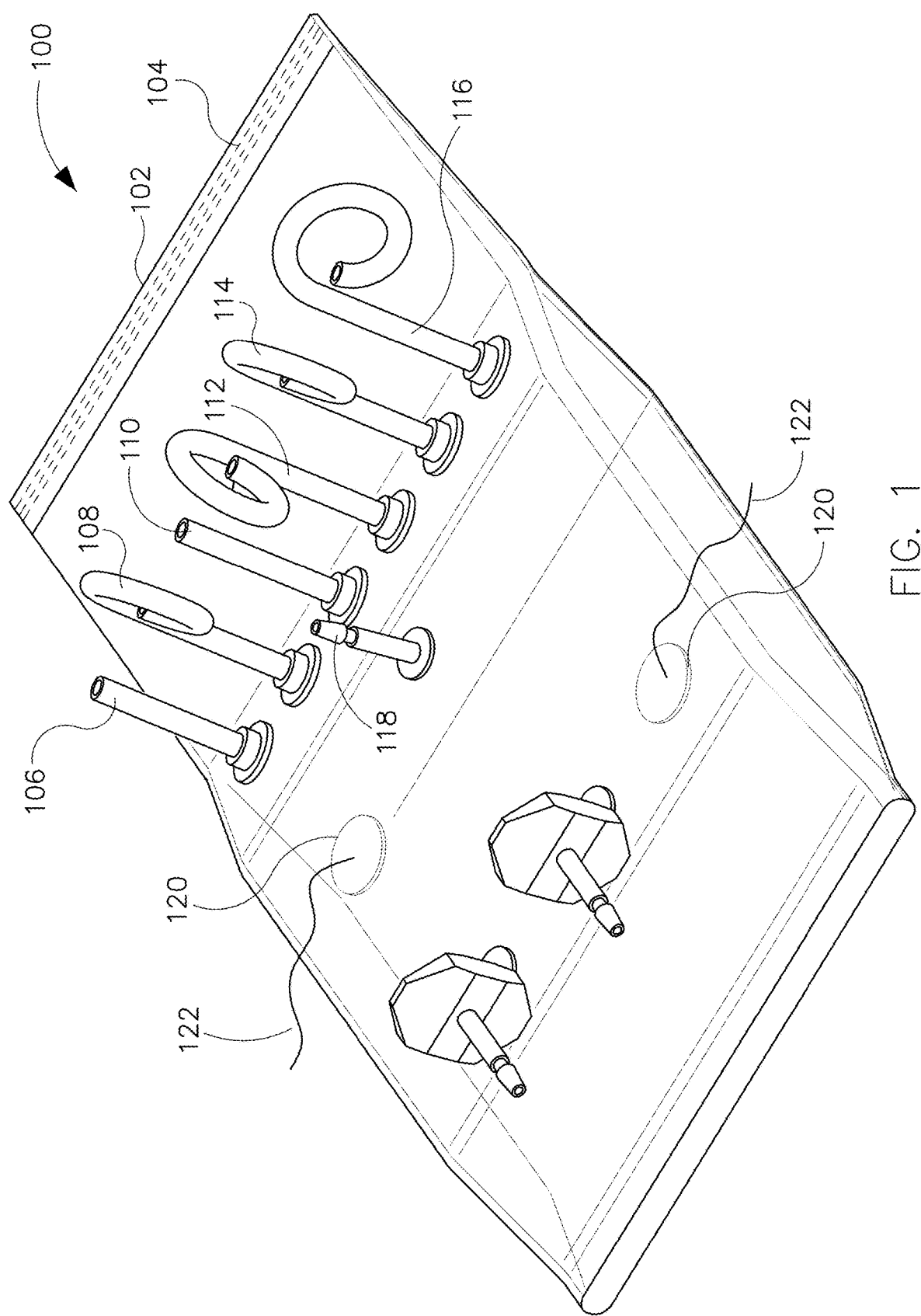
FIG. 1 is a top view of one embodiment of a container configured to hold a bone material and a coating material. The container is shown as a flexible container.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about." it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a." "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Biocompatible, as used herein, is intended to describe materials that, upon administration in vivo, do not induce undesirable long-term effects.

Bone, as used herein, refers to bone that is cortical, cancellous, or cortico-cancellous of autogenous, allogenic, xenogenic, or transgenic origin.

The term "autograft" refers to graft material harvested from the same individual patient who is also recipient of the graft, obtained surgically from non-essential donation sites in the patient.

Bone graft, as used herein, refers to any implant prepared in accordance with the embodiments described herein and therefore may include expressions such as a bone void filler.

The term "nano-sized feature" includes recesses, projections, or a combination thereof that are in nanometer size.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also can bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals including, without limitation, humans.

The term "implantable" as utilized herein refers to a biocompatible device (e.g., the composition) retaining potential for successful placement within a mammal. The expression "implantable composition" and expressions of the like as utilized herein refer to an object implantable through surgery, injection, or other suitable means whose primary function is achieved either through its physical presence or mechanical properties. An example of the implantable device is the composition.

The term "moldable" includes that the composition can be shaped by hand or machine or injected into the target tissue site (e.g., bone defect, fracture, or void) into a wide variety of configurations to fit within the bone defect.

The term "cohesive" as used herein means that the composition tends to remain a singular, connected mass upon the addition of fluid, autograft bone or during manipulation, including the exhibition of the ability to be molded or shaped without breaking upon manipulating, or disintegrating or becoming unstable.

The terms "macroparticle" or "macroform" include bone material that is visible to the naked eye. The bone material can be natural bone, synthetic bone material (e.g., demineralized bone, ceramic, etc.) or a combination thereof that is solid or semi-solid before hydration. Typically, the macroparticle can be from 0.01 mm to about 50 mm in length. It is to be understood that the terms macroparticle and macroform can be used interchangeably.

The term "flowable" includes that the composition can be administered in an injectable state via a syringe and/or cannula. The composition is flowable when its consistency is fluid-like and has a viscosity that is lower than that of the viscosity of the composition when in a putty or paste form. Flowable compositions include liquid or fluid (e.g., solution, suspension, or the like) or semi-solid compositions (e.g., gels, cements) that are easy to manipulate and may be brushed, sprayed, dripped, injected, shaped and/or molded at or near the target tissue site. "Flowable" includes compositions with a low viscosity or water-like consistency to those with a high viscosity, such as a paste-like material. In various embodiments, the flowability of the composition allows it to conform to irregularities, crevices, cracks, and/or voids in the bone defect site (e.g., bone void). For example, in various embodiments, the composition may be used to fill one or more voids in an osteolytic lesion.

The term "hydrate," "hydration." "hydratable," "hydrating' or "hydrated" refers to adding an amount of fluid to a composition to increase the amount of moisture content in the composition to form a putty or paste that is flowable.

The term "dehydrated" or "dehydration" refers to a composition that contains a small amount of residual moisture or no moisture content and can be in the form of a dry composition. The dehydrated composition can have a moisture content from about 0 to about 10% based on the total weight of the composition. In some embodiments, when a composition is dehydrated, fluid can be added to the composition to hydrate the composition. A dehydrated composition includes a lyophilized or freeze-dried composition.

The term "bone marrow aspirate" or "BMA" refers to the withdrawal of bone marrow fluid through a syringe and needle to harvest the bone marrow fluid from the patient. Bone marrow aspirate comprises fluid that contains a heterogeneous mix of stem and progenitor cells, platelets, and white blood cells. The bone marrow aspirate can be harvested from various sources in the body including, but not limited to, the iliac crest.

The term "soluble collagen" refers to the solubility of individual tropocollagen molecules in acidic aqueous environments. Tropocollagen may be considered the monomeric unit of collagen fibers and its triple helix structure is well recognized.

"Insoluble collagen" as used herein refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of an animal hide (e.g. bovine, porcine, fish, etc.) that is situated between the grain and the flesh sides.

Coating System

As illustrated in FIG. 1, a container 100 is provided. In some embodiments, the container comprises an opening 102 configured for adding bone material to be coated, a seal 104 configured to enclose the bone material in the interior of the container, an inlet configured to add a coating liquid to the interior of the container, an outlet configured to remove any excess coating material from the interior of the container, and a sensor 120 configured to sense or detect a parameter within the interior of the container. The parameters that the sensor can detect include, for example, temperature, pressure, weight, pH, humidity, air volume, flow volume, or the sensor can be a camera to visualize the coating environment. In some embodiments, the inlet comprises a liquid input 106, a gas input 108, and an optional or spare input 110. In some embodiments, the outlet comprises a liquid output 112, a gas output 114, and an optional or spare output 116. In some embodiments, the container also comprises a sensor output 122 configured to transfer the measurements collected by the sensor to a computer or a processor. In some embodiments, the container comprises a sampling inlet 118 configured for a user to collect a sample of the bone material, a sample of the coating material, and/or a sample of the mixture of the two to test its contents.

Figure 2:
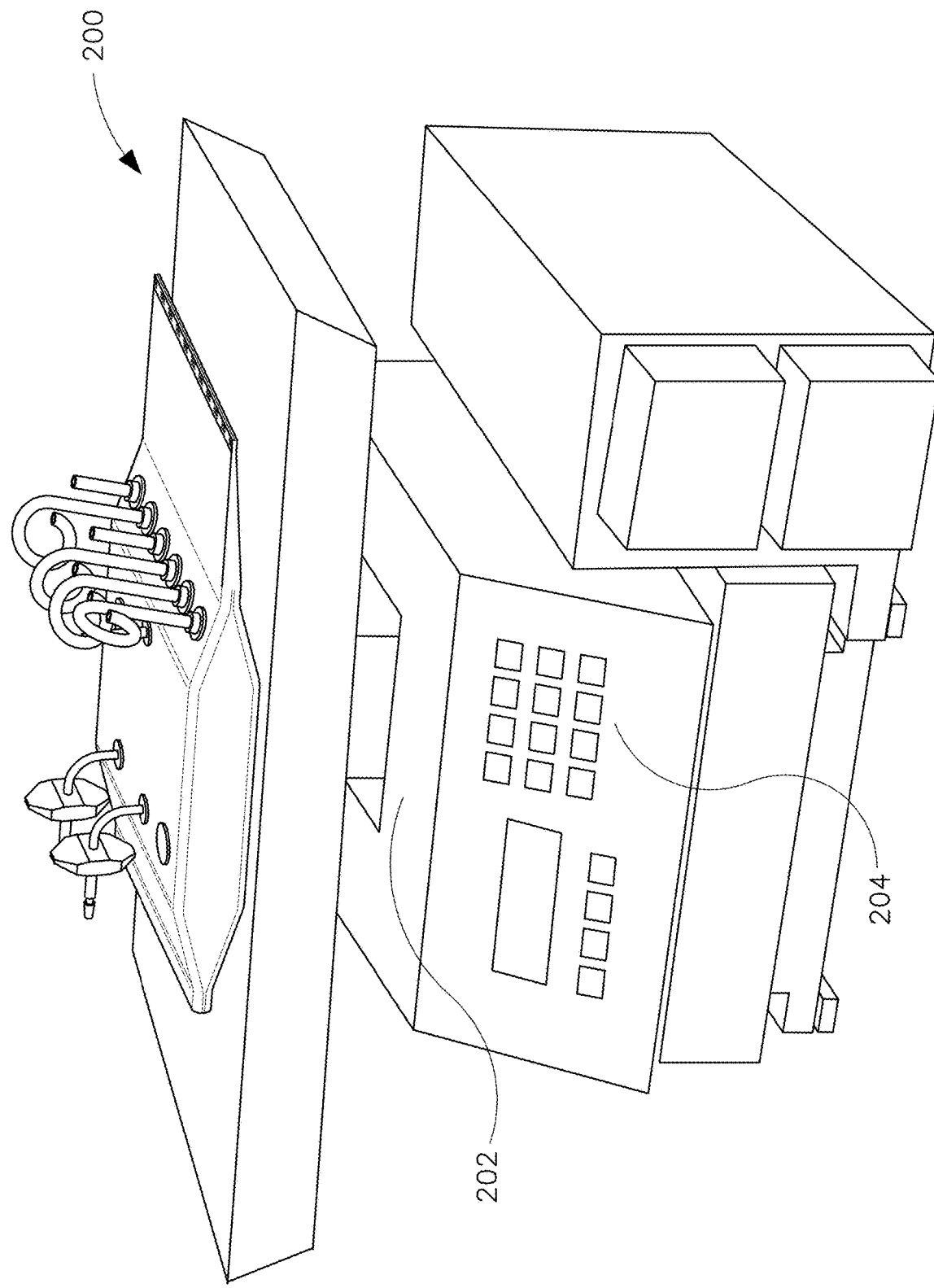
FIG. 2 is a perspective view of one embodiment of a reactor contacting a balance and coupled to a heating element.

In some embodiments, the container is placed on a reactor 200, as shown in FIG. 2. The reactor 200 is configured to receive and hold the container, the reactor having a balance 202 configured to move and tilt one end in a vertical direction causing a rocking motion of the balance and a wave motion to the mixture in the interior of the container to allow contact and coating of the bone material; and a heating element 204 configured to heat up and maintain the temperature of the container and the mixture inside the container. In some embodiments, the container is placed on a balance configured to measure the weight of the bag allowing control of addition or removal of the coating material or second coating material from the interior of the container. Therefore, a desired amount of coating material can be added to the bag and measured based upon its weight. The coating material can also be removed or added until the desired weight is reached.

Figure 3A:
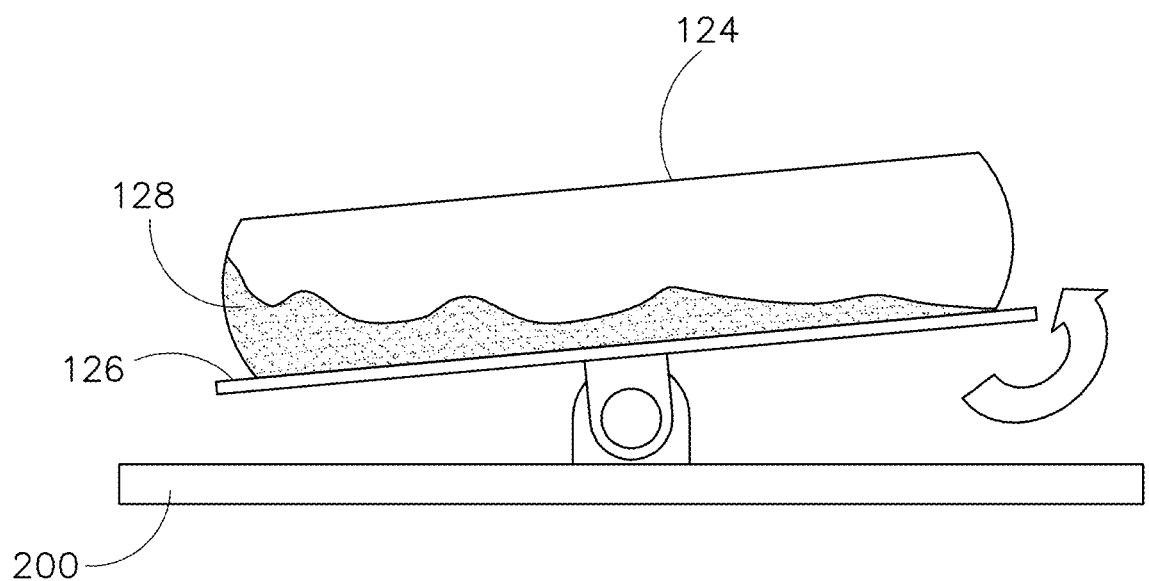
FIG. 3A is a front view of one embodiment of a container placed on a reactor. The balance is having a rocking motion at one end of the balance so as to mix components to coat the bone material.
Figure 3B:
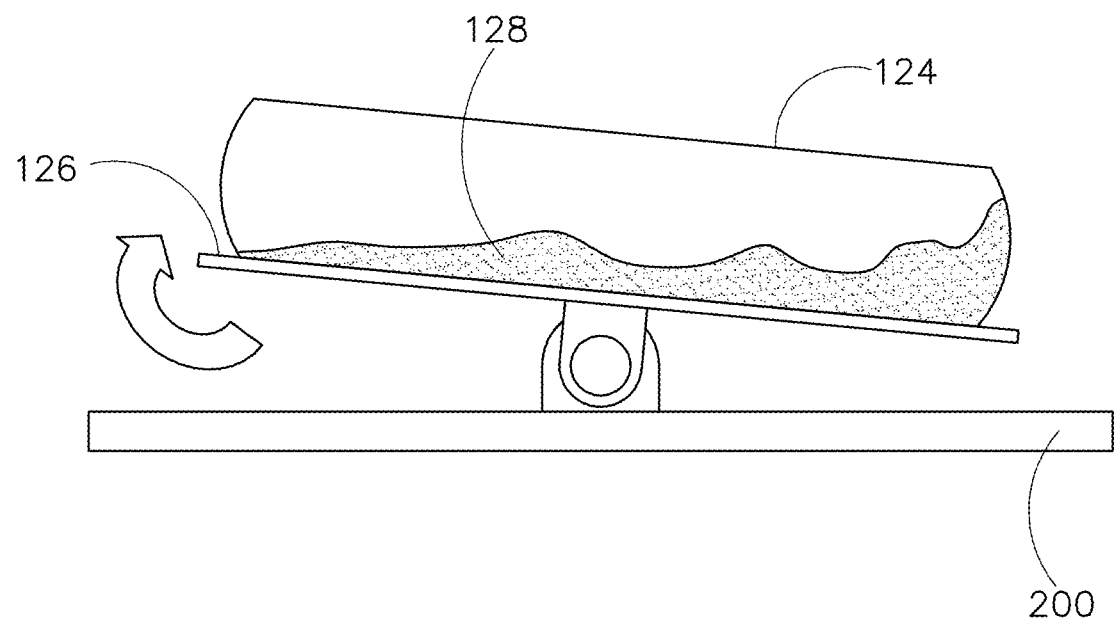
FIG. 3B is a front view of another embodiment of a container placed on a reactor. The balance is having a rocking motion at one end of the balance to coat the bone material.
Figure 4:
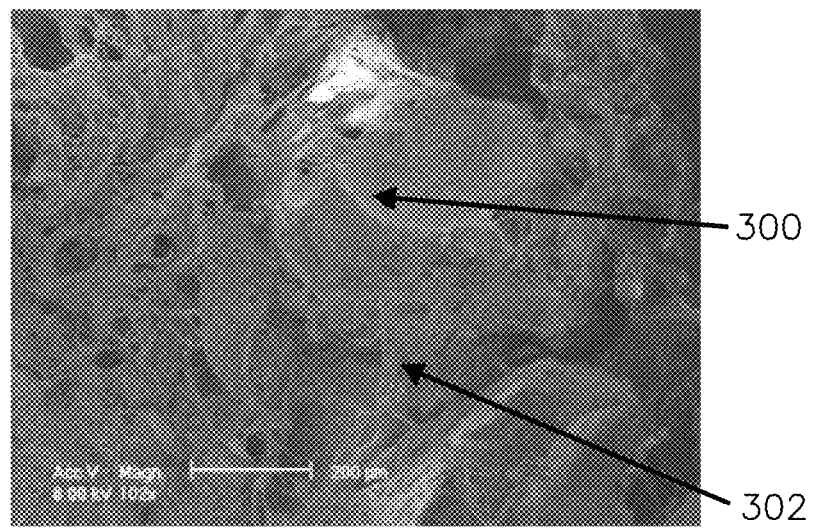
FIG. 4 is a scanning electron microscope (SEM) micrograph of a coated bone material having a nanometer size coating and nanometer size structure.
Figure 5:
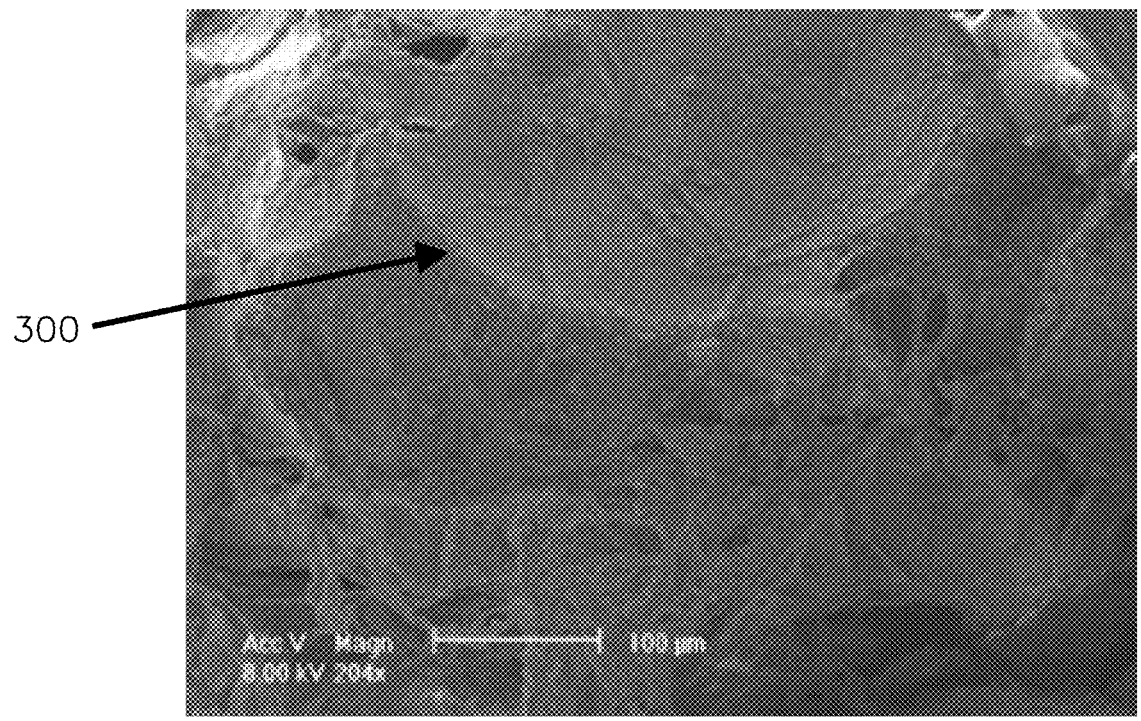
FIG. 5 is another scanning electron microscope (SEM) micrograph of a coated bone material having a nanometer size coating and nanometer size structure.
Figure 6:
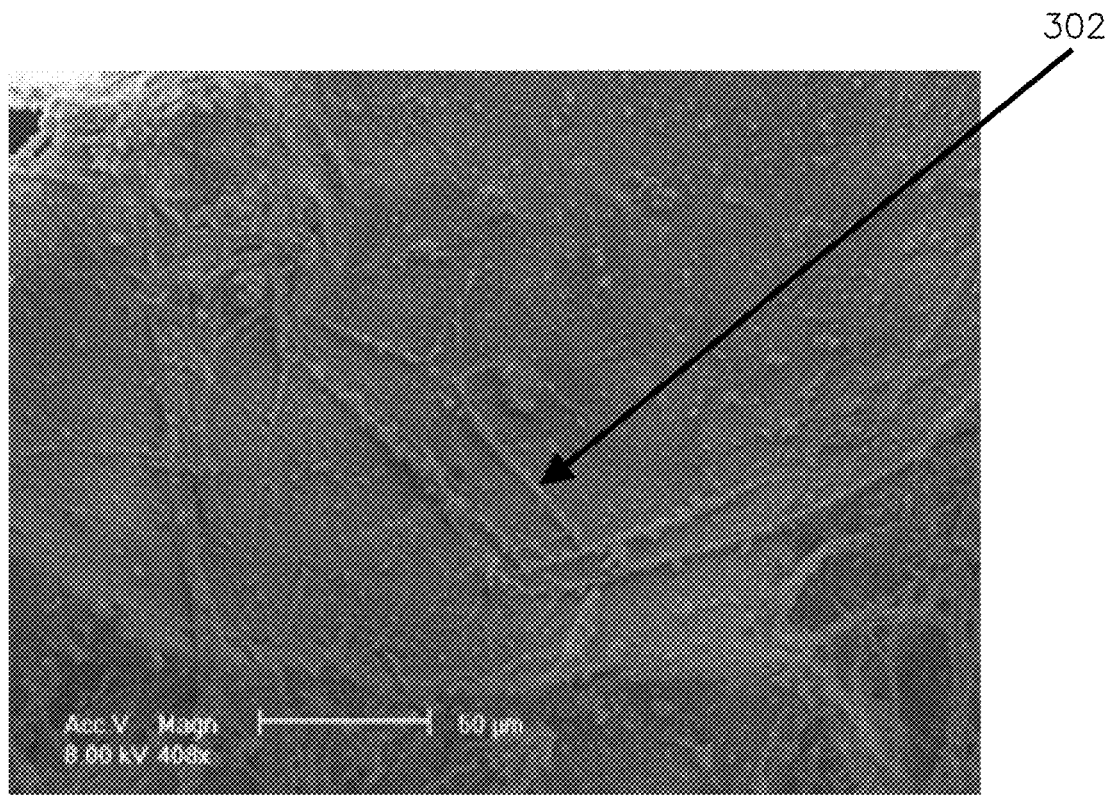
FIG. 6 is another scanning electron microscope (SEM) micrograph of a coated bone material having a nanometer size coating and nanometer size structure.
Figure 7:
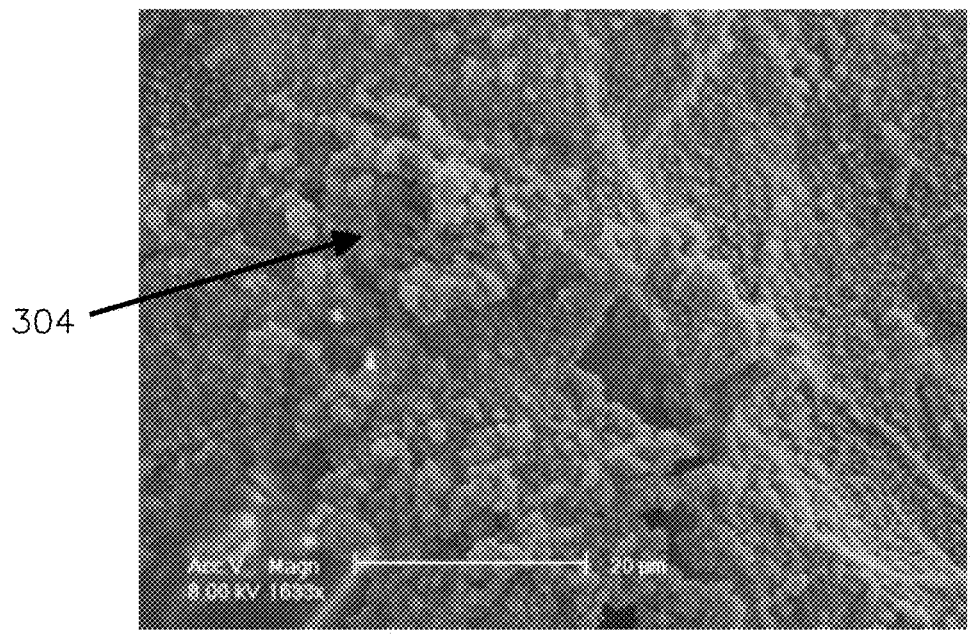
FIG. 7 is a scanning electron microscope (SEM) micrograph of a coating material having a nanometer size coating and nanometer size structure.

FIGS. 3A and 3B illustrate the rocking motions of the balance. The container having a bottom surface 126 disposed on the top of the balance. In some embodiments, the container has a top surface 124 having the inlet, outlet, and the sensor. The reactor 200 has a rocking motion AA on the balance at one end to cause the bone material and the coating material to form a wave in the interior of the container, thus mixing the bone material and the coating material together into a mixture 128 facilitating the coating on the bone material. The balance can also tilt to an opposite end causing a rocking motion BB in different direction. These two rocking motions in the balance can cause a wave motion inside the container, which facilitates the mixing of the bone material and the coating material allowing the coating material to distribute on the bone material evenly. In some embodiments, after the coating material or second coating material is added to the container, the container is placed on the balance such that the movement of the balance mixes the bone material and the liquid coating material and/or the second liquid coating material. In some embodiments, the balance also measures the weight of the bag disposed on the top of the balance. The weight measured by the balance allows a processor to automate the addition and removal of the coating materials. In some embodiments, the mixture comprises the bone material and the coating material; the bone material in the mixture can be non-coated, partially coated or fully coated. In some embodiments, the mixture comprises other non-coating materials such as sterilized saline, sterilized water and sterilized air that are configured to adjust the temperature, the pH of the mixture or the pressure of the container.

Figure 8:
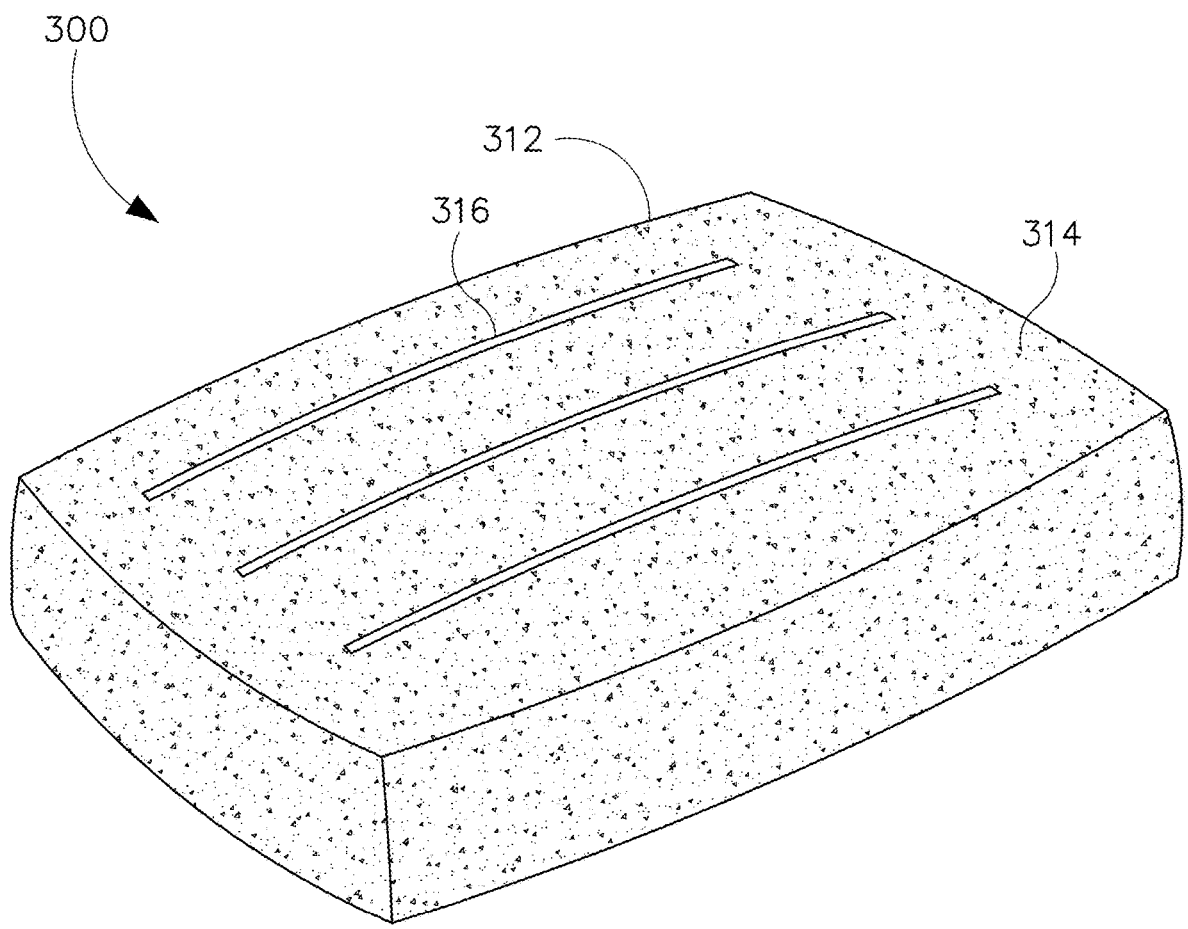
FIG. 8 is a perspective view of one embodiment of coated bone material. The bone material is coated, and the coating imparts a plate-like structure and a carbonate-substituted, calcium deficient hydroxyapatite phase to the bone material.

FIGS. 4-7 illustrate a scanning electron microscope (SEM) micrograph of the end product after the coating process. The end product comprises the coated bone material 300 including coated collagen 302 and coating material 304 disposed on top of the bone material. In some embodiments, the coated bone material 300 can have a molded shape 312, as shown in FIG. 8. In some embodiments, the shape is circular, triangular, polygonal, or a custom shape designed for the need to repair a bone defect. In some embodiments, the coated bone material has channels 316 and porous macroparticles 314.

Figure 9:
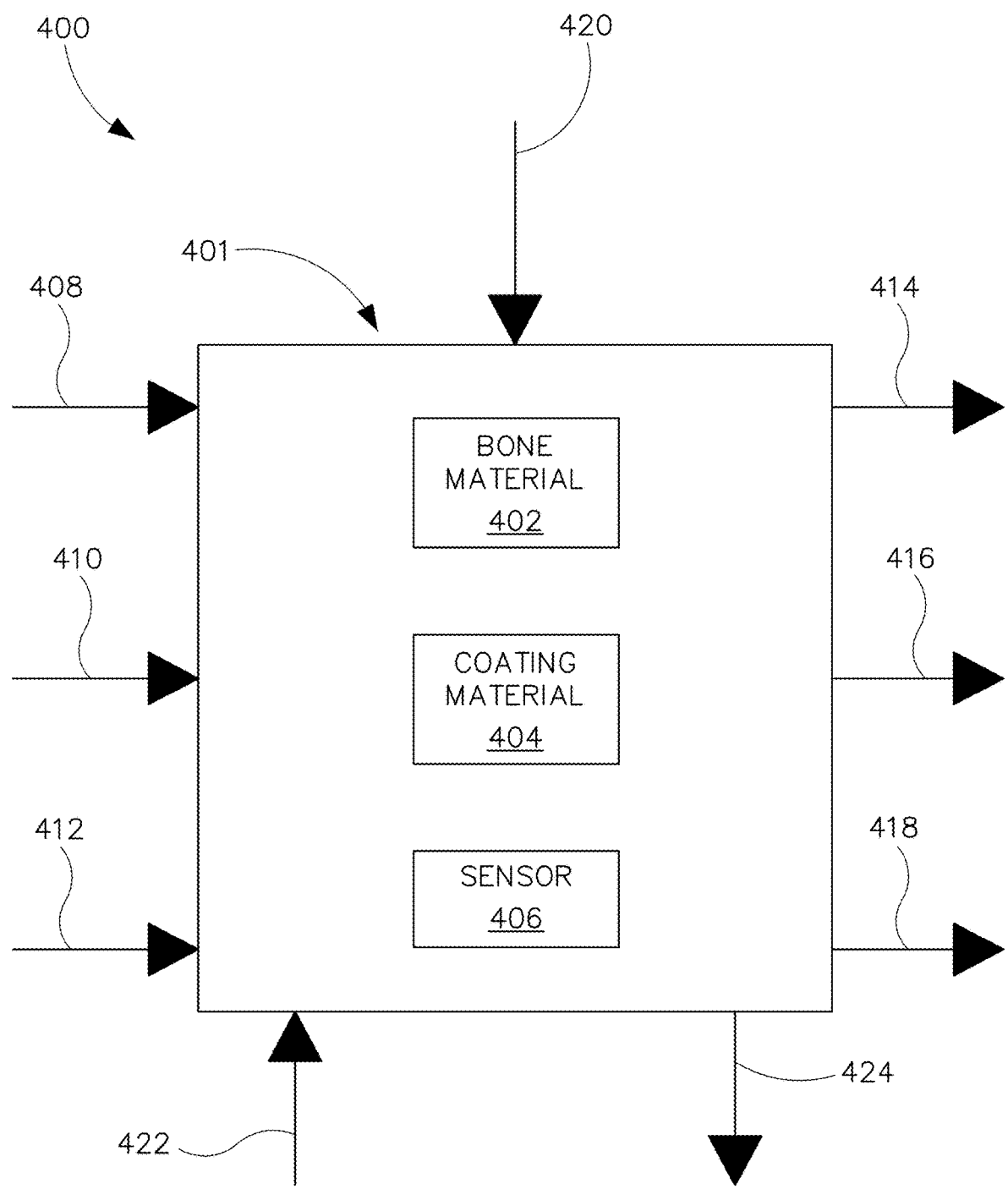
FIG. 9 is a system diagram for the container, the bone material, and the coating material.
Figure 11:
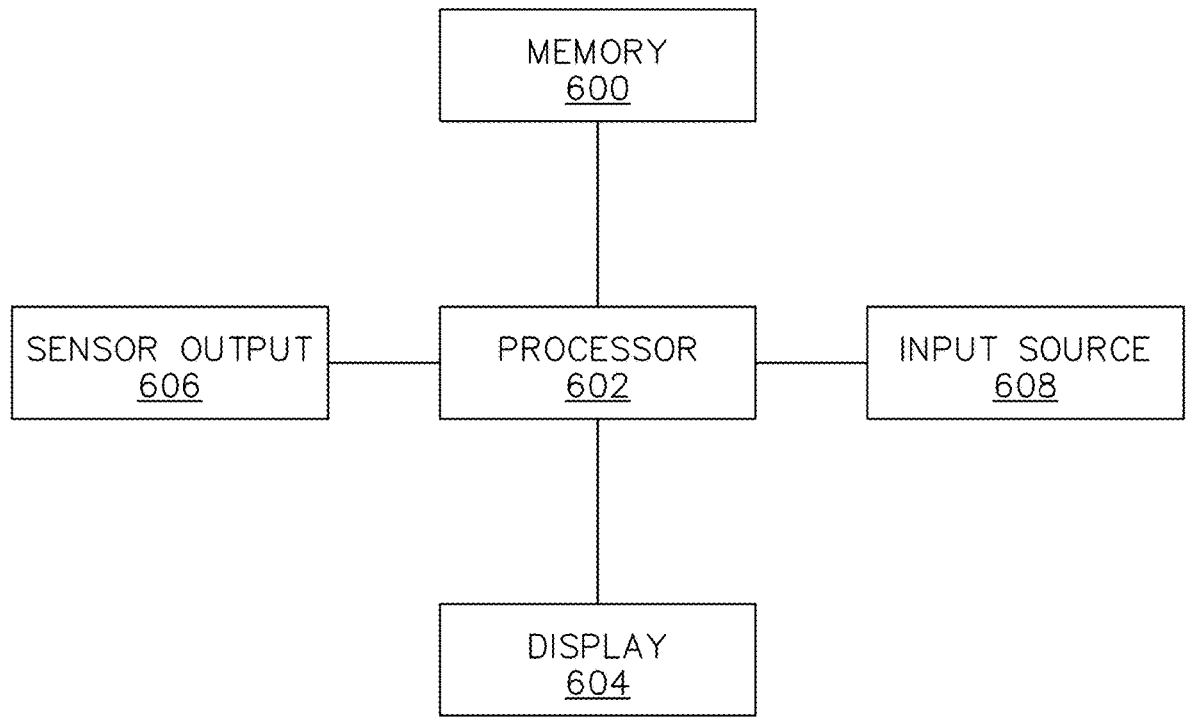
FIG. 11 illustrates an embodiment of a computer-implemented system for coating a bone material.

FIG. 9 illustrates another embodiment of the system for the coating bone material. The system 400 comprises container 401, bone material 402, coating material 404, sensor 406 and a computer, which is depicted in FIG. 11. The sensor can be, for example, a temperature sensor, a pressure sensor, a pH sensor, a humidity sensor, a weight sensor, liquid flow sensor, air flow sensor, or an optical sensor or there can be one sensor 406 that detects all of these parameters and other parameters. The system is configured to have liquid input 408, gas input 410 and spare input 412 configured to deliver additional or separate coating or bone materials from other inputs such as a non-coating related liquid or gas. In some embodiments, the liquid input, the gas input, and the spare input are a plurality of inlet ports disposed on the container. The system is also configured to have liquid output 414, gas output 416 and spare output 418 configured to drain or remove the bone material, the coating material, or other undesirable material from the container. In some embodiments, the liquid output, the gas output, and the spare output are a plurality of outlet ports disposed on the container. In some embodiments, the input such as the liquid input, the gas input, or the spare input, comprises a plurality of the inputs and are configured to have the same or different concentration or materials to be delivered simultaneously or in specific time arrangement. The output has the similar setup. In some embodiments, the system is configured to have an entryway 420 for solid input and output. In some embodiments, the solid input and output is an opening on the container. In some embodiments, the system is configured to have a thermo and balance input 422. In some embodiments, the thermo input and the balance input are on a reactor having a balance and a heating element. In some embodiments, the sensor is connected to sensor output 424, which transfers the information to the computer, or directly to the reactor. In some embodiments, the input and the output comprise an on/off switch configured to be controlled by the computer. In some embodiments, the inlet comprises a port disposed on the top surface of the container and a tubing connected to source material. In some embodiments, the source material is a coating material held in a chamber configured to allow the coating material to pass from the chamber to the container of the bone material through the tubing and the port. Similarly, an outlet comprises a port and a tubing allowing the removed of the coating material to be transferred to a separate container or chamber.

Figure 10:
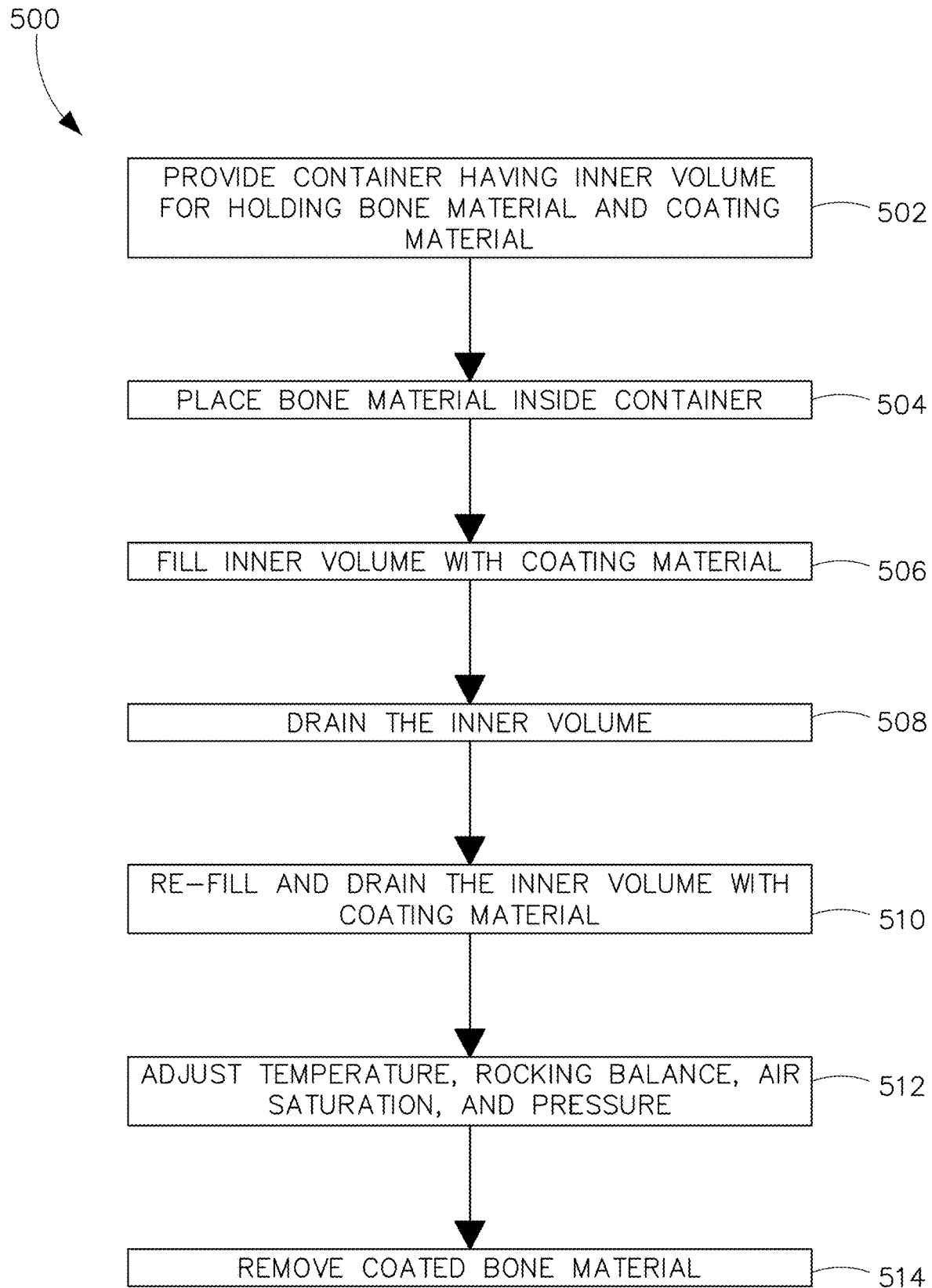
FIG. 10 is a flow diagram illustrating an embodiment of the system for coating a bone material.

As shown in FIG. 10, a method 500 for coating bone material is illustrated. In a first step 502, a container having an inner volume for holding bone materials and coating material is prepared. In some embodiments, the container is in the form of a disposable and flexible bag. In some embodiments, the container is in the form of a non-disposable and flexible bag. In some embodiments, the container comprises more sturdy material allowing the container to be used repeatedly and withstand sterilization processes. In some embodiments, the container is sterilized before the coating process and maintains its sterility throughout the coating process. In some embodiments, the container is not sterilized. In a second step 504, a bone material ready for coating is placed inside the container. In some embodiments, the bone material is sterilized and maintains its sterility throughout the coating process. In a third step 506, coating material is imported into the inner volume of the container. In some embodiments, the coating material flows into the container in one or more inlet ports at the same time or at different time and rates. In a fourth step 508, after a certain time period, the excess coating material is drained or removed from the container throughout an outlet. In a fifth step 510, coating material is imported into the inner volume of the container and drained from the inner volume of container as in the third and the fourth steps. The fifth step can be repeated until all desired coating materials including the primer composition and desired layers are achieved. In a sixth step 512, a sensor from the container sends the measurements of temperature, balance, air saturation, pressure and imaging of the bone material and the coating material to a computer; then a computer adjusts the temperature, the balance, the air saturation, and pressure to a desired condition for coating. Pressure can be adjusted through addition of sterilized air or suitable gas via an inlet such as a gas input or a spare input. Pressure also can be adjusted via an outlet to a suction source or a vacuum.

Pressure can be measured through a pressure sensor or an optical sensor that can image the coating environment in the interior or exterior of the container. In some embodiments, the container comprises a pressure sensor and the method further comprises measuring the pressure inside the container and adjusting the pressure inside the container to a selected pressure. In some embodiments, the method comprises manually mixing the bone material and the liquid coating material in the interior of the container to form a mixture. In some embodiments, the mixing can be an automated mixing process. There is no specific or particular order to the sequence of the steps including the sixth step, as the sixth step can be executed at any time during the coating process. In a seventh step 514, the coated bone material is removed from the container as the coating process is completed. The coated bone material is sterile and does not require end product sterilization before use.

In some embodiments, a bone material comprising a scaffold is provided and placed in an interior of a sterilized container through an opening. The opening is then sealed, and the container is placed on top of a balance of a reactor. An inlet comprising a liquid input port is switched on and a primer composition is delivered into the interior of the container and the inlet is switched off after the primer composition has filled the container or has delivered a desired amount. A sensor is connected to a computer and the reactor allows the temperature, the pH and the pressure of the system to be adjusted for the coating conditions. The scaffold is then coated and incubated. When the incubation time period is finished, the excess primer composition is then drained through an outlet as the outlet will be switched on. In some embodiments, any excess gas byproduct or impurity can be filtered out through a gas outlet. The coating material including the simulated body fluid having mineral content is then filled into the container and drained after the incubation period. In some embodiments, multiple coatings are applied through repetition of the above steps. The mineralized coated scaffold is then removed from the container through the opening. The mineralized coated scaffold does not require additional processing or sterilization as the coating process is done aseptically. In some embodiments, the removal of the coated bone material is completed through automation by a mechanism arm to further prevent human manipulation and potential contamination of the coated bone material.

As illustrated in FIG. 11, a computer is provided, the computer comprising processor 602 comprises logic to execute one or more instructions from the reactor (for example, balance's rocking motions or the heating elements). The logic for executing instructions may be encoded in one or more tangible media for execution by the processor. For example, the processor may execute codes stored in a computer-readable medium such as memory 600. The computer-readable medium may be stored in, for example, electronic (for example, RAM (random access memory), ROM (read-only memory), EPROM (erasable programmable read-only memory), magnetic, optical (for example, CD (compact disc), DVD (digital video disc)), electromagnetic, semiconductor technology, or any other suitable medium. The computer includes logic to calculate the desired conditions for particular coating materials and bone materials. The execution of specific instructions are carried out by an input source to the coating system (for example, liquid input, gas input, thermo or temperature input and balance input, etc.). The computer allows the entire coating process discussed above to be automated and controlled by a machine without a required of human manipulation on the bone materials and/or coating materials.

The user can interface with the computer via a user interface that may include one or more display devices 604 (for example, CRT, LCD, touch screen, or other known displays) or other output devices (for example, printer, etc.), and one or more input devices (for example, keyboard, mouse, stylus, touch screen interface, or other known input mechanisms) for facilitating interaction of a user with the system via user interface. The user interface may be directly coupled to a database or directly coupled to a network server system via the Internet, WiFi or cloud computing. In accordance with one embodiment, one or more user interfaces are provided as part of (or in conjunction with) the illustrated systems to permit users to interact with the systems.

The user interface device may be implemented as a graphical user interface (GUI) containing a display 604 or the like, or may be a link to other user input/output devices known in the art. Individual ones of a plurality of devices (for example, network/stand-alone computers, personal digital assistants (PDAs), WebTV (or other Internet-only) terminals, set-top boxes, cellular phones, screen phones, pagers, blackberry, smart phones, iPhone, iPad, tablet, peer/non-peer technologies, kiosks, or other known (wired or wireless) communication devices, etc.) may similarly be used to execute one or more computer programs (for example, universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (for example, the Internet).

The database can be stored in storage devices or systems (for example, Random Access Memory (RAM), Read Only Memory (ROM), hard disk drive (MD), floppy drive, zip drive, compact disk-ROM, DVD, bubble memory, flash drive, redundant array of independent disks (RAID), network accessible storage (NAS) systems, storage area network (SAN) systems, e CAS (content addressed storage) may also be one or more memory devices embedded within a CPU, or shared with one or more of the other components, and may be deployed locally or remotely relative to one or more components interacting with the memory or one or more modules. The database may include a data storage device, a collection component for collecting information from users or other computers into a centralized database, a tracking component for tracking information received and entered, a search component to search information in the database or other databases, a receiving component to receive a specific query from a user interface, and an accessing component to access centralized database. A receiving component is programmed for receiving a specific query from one of a plurality of users. The database may also include a processing component for searching and processing received queries against a data storage device containing a variety of information collected by a collection device such as a sensor and transferred to the processor via sensor output 606, which includes wires, wireless and network connections as discussed below.

The disclosed system may, in some embodiments, be a computer network-based system. The computer network may take any wired/wireless form of known connective technology (for example, corporate or individual LAN, enterprise WAN, intranet, Internet, Virtual Private Network (VPN), combinations of network systems, etc.) to allow a server to provide local/remote information and control data to/from other locations (for example, other remote database servers, remote databases, network servers/user interfaces, etc.). In accordance with one embodiment, a network server may be serving one or more users over a collection of remote and disparate networks (for example, Internet, intranet, VPN, cable, special high-speed ISDN lines, etc.). The network may comprise one or more interfaces (for example, cards, adapters, ports) for receiving data, transmitting data to other network devices, and forwarding received data to internal components of the system (for example, input and output switch, heating element, balance motion and position, etc.) such that the system executes the necessary component via an input source 608. In some embodiments, the input source can be an inlet for a primer composition to increase the volume. In some embodiment, the input source can be an outlet to drain the excess coating materials. In some embodiments, the input source can be a heating element to elevate or maintain the temperature.

In accordance with one embodiment of the present application, the data may be downloaded in one or more textual/graphical formats (for example, RTF, PDF, TIFF, JPEG, STL, XML, XDFL. TXT etc.), or set for alternative delivery to one or more specified locations (for example, via e-mail, etc.) in any desired format (for example, print, storage on electronic media and/or computer readable storage media such as CD-ROM, etc.). The user may view the search results and underlying documents at the user interface, which allows viewing of one or more documents on the same display 604.

Bone Materials

The bone material can be solid, semi-solid, or liquid form. The bone material can be in granular, paste, putty or powder forms. In some embodiments, the bone material can be demineralized bone material. The demineralized bone material can comprise demineralized bone, powder, chips, granules, shards, fibers or other shapes having irregular or random geometries. These can include, for example, substantially demineralized, partially demineralized, or fully demineralized cortical and cancellous bone. These also include surface demineralization, where the surface of the bone construct is substantially demineralized, partially demineralized, or fully demineralized, yet the body of the bone construct is fully mineralized. The configuration of the bone material can be obtained by milling, shaving, cutting or machining whole bone as described in, for example, U.S. Pat. No. 5,899,939. The entire disclosure is herein incorporated by reference into the present disclosure.

In some embodiments, the bone material can comprise elongated demineralized bone fibers having an average length to average thickness ratio or aspect ratio of the fibers from about 50:1 to about 1000:1. In overall appearance the elongated demineralized bone fibers can be round, spherical, granular, elongated, powders, chips, fibers, cylinders, threads, narrow strips, thin sheets, or a combination thereof. In some embodiments, the bone material comprises elongated demineralized bone fibers and chips. In some embodiments, the bone material comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the bone material comprises demineralized bone matrix fibers and demineralized bone matrix chips in a 30:60 ratio. In some embodiments, the bone material comprises demineralized bone matrix fibers and demineralized bone matrix chips in a ratio of 25:75 to about 75:25 fibers to chips.

In some embodiments, the bone material can be an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the bone material can comprise mineral particles, which comprise tricalcium phosphate and hydroxyapatite in a ratio of about 80:20 to about 90:10. In some embodiments, the mineral particles can comprise tricalcium phosphate and hydroxyapatite in a ratio of about 70:30 to about 95:5. In some embodiments, the mineral particles can comprise tricalcium phosphate and hydroxyapatite in a ratio of about 85:15.

In some embodiments, the bone material may be seeded with harvested bone cells and/or bone tissue, such as for example, cortical bone, autogenous bone, allogenic bones and/or xenogeneic bone while it is mixed.

In some embodiments, the bone material may be mixed with one or more therapeutic agents, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof. Recombinant BMP-2 can be used at a concentration of about 0.4 mg/mL to about 10.0 mg/mL, preferably about 1.5 mg/mL.

The bone material may include or be mixed with one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The bone material may include or be mixed with a therapeutic agent including, but not limited to, IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. The bone material may include or be mixed with therapeutic agents including excitatory amino acids such as glutamate and aspartate, antagonists or inhibitors of glutamate binding to NMDA receptors, AMPA receptors, and/or kainate receptors. The bone material may include or be mixed with therapeutic agents to reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

The bone material may include or be mixed with a therapeutic agent including, but not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The bone material may include or be mixed with a therapeutic agent including, but not limited to, an anti-inflammatory agent. An example of an anti-inflammatory agent includes, but is not limited to, clonidine, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The bone material may include or be mixed with a therapeutic agent including, but not limited to, a statin. Examples of a useful statin include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the bone material can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium;

cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; crythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

The antimicrobial agent in the bone material can be an antiviral agent that can be mixed with the bone material. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddl (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Mineral Coating

A bone material, including a scaffold, or portion or component thereof, described herein can include a surface modification or a coating. The mineral coating of a scaffold, as described herein, can be performed by any conventional manner. A mineral coating can be as described in U.S. application Ser. Nos. 13/407,441; 13/879,178; and 13/036,470 and are incorporated by reference.

In some embodiments, there are exemplary methods for producing coated scaffolds (e.g., bone material) using a mineral coating solution. For example, the mineral coating solution can be a modified simulated body fluid (mSBF). By adjusting the mineral composition, and/or concentration of the mSBF, the composition of the mineral precipitated on the scaffolds can be manipulated. See also U.S. Patent Publication No. US 2008/0095817 A1; U.S. Pat. No. 6,767,928 B1. U.S. Pat. No. 6,541,022 B1, PCT Publication WO 2008/070355 A2; PCT Publication WO 2008/082766 A2; Murphy and Mooncy, 2001; and Murphy and Messersmith, 2000.

As described herein, the mineral coating can be calcium-containing. For example, the calcium-containing mineral coating can include hydroxyapatite (HAP), α-tricalcium phosphate (α-TCP), β-tricalcium phosphate (β-TCP), amorphous calcium phosphate, dicalcium phosphate, octacalcium phosphate, calcium phosphate (CaP), or calcium carbonate. The calcium-containing mineral coating can comprise a plurality of layers, e.g., separate layers having distinct dissolution profiles. Under physiological conditions, solubility of calcium phosphate species can adhere to the following trend: amorphous calcium phosphate>dicalcium phosphate>octacalcium phosphate>β-TCP>HAP. A dicalcium phosphate mineral can have a dissolution rate that is more than fifty times higher than that of HAP. Therefore, creation of a matrix with distinct calcium phosphate layers allows for a broad range of dissolution patterns.

For example, a mineral coating can be according to ISO 2337 'Implants for surgery-In vitro evaluation for apatite-forming ability of implant materials.' As another example, a mineral coating can be an adapted protocol according to ISO 2337 'Implants for surgery-In vitro evaluation for apatite-forming ability of implant materials.' As another example, the mineral coating can be performed by immersing a scaffold into a modified simulated body fluid at physiological conditions and continuous rotations. Continuous rotations can replenish the modified simulated body fluid, replace the modified simulated body fluid, or remove and add modified simulated body fluid.

As described herein, the scaffold can be incubated in modified simulated body fluid (mSBF) solutions to induce formation of a calcium phosphate-based mineral layer for mineral nucleation and growth. The mSBF solution can contain ionic constituents of blood plasma, with double the concentrations of calcium and phosphate ions, held at physiologic temperature and pH. The growth of calcium phosphate-based minerals, specifically bone-like minerals, on bioresorbable polymer matrices using mSBF incubation has been demonstrated (Lin et al., 2004; Murphy et al., 2002, 2005).

As described herein, a mineral coating of a scaffold, as described herein, can be performed by incubating a scaffold. For example, the mineral coating, described herein, can be developed by incubating the constituents in modified simulated body fluid (mSBF), between 3-4 days or less at a pH of about 6.8 to about 7.4 and at a temperature of about 25° C. to about 37° C. The SBF or mSBF can be refreshed daily. Using the chemical composition, the procedure produces a calcium-deficient, carbonate-containing apatite material on alginate and on poly-(α-hydroxy esters). Sec U.S. Pat. No. 6,767,928, incorporated herein by reference. mSBF can include elevated calcium and phosphate. In general, an increase in pH can favor hydroxyapatite growth, while a decrease in pH can favor octacalcium phosphate mineral growth.

As another example, conditions favorable for hydroxyapatite formation can include a pH between about 5.0 and about 8.0 and a calcium concentration multiplied by a phosphate concentration between about 10-5 and about 10-8 M. Likewise, conditions favorable for octacalcium phosphate formation include a pH between about 6.0 and about 8.0 and a calcium concentration multiplied by a phosphate concentration between about 10-5 and about 10-7.5 M. Furthermore, conditions favorable for dicalcium phosphate dehydrate formation can include a pH between about 6.0 and about 8.0 and a calcium concentration multiplied by a phosphate concentration between about 10-4 and about 10-6 M.

As another example, one could vary the pH of mSBF between about 5.0 and about 6.0 to promote hydroxyapatite formation. Similarly, one could vary the pH of mSBF between about 6.0 and about 6.5 to promote octacalcium phosphate and hydroxyapatite formation. Likewise, one could vary the pH of mSBF between about 6.5 and about 8.0 to promote dicalcium phosphate, octacalcium phosphate, and hydroxyapatite formation.

As another example, the scaffold can be incubated for at least about 1 day; at least about 2 days; at least about 3 days; at least about 4 days; at least about 5 days; at least about 6 days; at least about 7 days; at least about 8 days; at least about 9 days; at least about 10 days; at least about 11 days; at least about 12 days; at least about 13 days; at least about 14 days; at least about 15 days; at least about 16 days; at least about 17 days; at least about 18 days; at least about 19 days; at least about 20 days; at least about 21 days; at least about 22 days; at least about 23 days; at least about 24 days; at least about 25 days; at least about 26 days; at least about 27 days; at least about 28 days; at least about 29 days; or at least about 30 days. It is understood that recitation of the above discrete values includes a range between each recited value.

For example, the scaffold can be incubated for about 1 day; about 2 days; about 3 days; about 4 days; about 5 days; about 6 days; about 7 days; about 8 days; about 9 days; about 10 days; about 11 days; about 12 days; about 13 days; about 14 days; about 15 days; about 16 days; about 17 days; about 18 days; about 19 days; about 20 days; about 21 days; about 22 days; about 23 days; about 24 days; about 25 days; about 26 days; about 27 days; about 28 days; about 29 days; or about 30 days. It is understood that recitation of the above discrete values includes a range between each recited value.

A mineral coating of a scaffold, as described herein, can be performed by incubating a scaffold at a temperature. For example, the scaffold can be incubated at a physiologically relevant temperature. As another example, the scaffold can be incubated at a temperature of about 1° C.; about 2° C.; about 3° C.; about 4° C.; about 5° C.; about 6° C.; about 7° C.; about 8° C.; about 9° C.; about 10° C.; about 11° C.; about 12° C.; about 13° C.; about 14° C.; about 15° C.; about 16° C.; about 17° C.; about 18° C., about 19° C., about 20° C., about 21° C.; about 22° C.; about 23° C.; about 24° C.; about 25° C.; about 26° C.; about 27° C.; about 28° C.; about 29° C.; about 30° C.; about 31° C.; about 32° C.; about 33° C.; about 34° C.; about 35° C.; about 36° C.; about 37° C.; about 38° C.; about 39° C.; about 40° C.; about 41° C.; about 42° C.; about 43° C.; about 44° C.; about 45° C.; about 46° C.; about 47° C.; about 48° C.; about 49° C.; about 50° C.; about 51° C.; about 52° C.; about 53° C.; about 54° C.; about 55° C.; about 56° C.; about 57° C.; about 58° C.; about 59° C.; about 60° C.; about 61° C.; about 62° C.; about 63° C.; about 64° C.; about 65° C.; about 66° C.; about 67° C.; about 68° C.; about 69° C.; about 70° C.; about 71° C.; about 72° C.; about 73° C.; about 74° C.; about 75° C.; about 76° C.; about 77° C.; about 78° C.; about 79° C.; about 80° C.; about 81° C.; about 82° C.; about 83° C.; about 84° C.; about 85° C.; about 86° C.; about 87° C.; about 88° C.; about 89° C.; about 90° C.; about 91° C.; about 92° C.; about 93° C.; about 94° C.; about 95° C.; about 96° C.; about 97° C.; about 98° C.; about 99° C.; or about 100° C. It is understood that recitation of the above discrete values includes a range between each recited value.

A scaffold, or portion or component thereof, can be coated individually or in groups using, for example, a CaP coating technology. A scaffold, or portion or component thereof, can be modified individually or in groups using a technique such as aminolysis for RGD attachment, chemical conjugation, layer by layer deposition, or chemical vapor deposition.

Prior to deposition of the first calcium-containing mineral, the scaffold may be surface-functionalized to allow increased mineral deposition by utilizing chemical pre-treatment to achieve surface hydrolysis (e.g., using an NaOH solution). Surface degradation by this technique can cause an increase in the amount of polar oxygen functional groups on the surface of the material.

The functionalized surface can then be incubated in a mineral-containing solution (e.g., modified simulated body fluid). The mineral coating process, as described herein, can mimic natural biomineralization processes.

The mineral coating, as described herein, can be similar in structure and composition to human bone mineral. For example, the mineral coating can include spherical clusters with a plate-like structure or a plate-like structure and a carbonate-substituted, calcium deficient hydroxyapatite phase composition. As another example, the coating can be an osteoconductive mineral coating.

As another example, the mineral coating can include an apatite. Apatite can include calcium phosphate, calcium carbonate, calcium fluoride, calcium hydroxide, or citrate.

As another example, a mineral coating can comprise a plurality of discrete mineral islands on the scaffold, or the mineral coating can be formed on the entire surface of the scaffold. As another example, the mineral coating can comprise a substantially homogeneous mineral coating. In other embodiments, the mineral coatings can be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, or a mixture thereof. For example, an osteoconductive mineral coating can be calcium-deficient carbonate-containing hydroxyapatite.

As another example, the mineral coating can include hydroxyapatite. Calcium deficient hydroxyapatite can have a formula of $Ca_{10-x}(PO_4)_{6-x}(HPO_4)_x(OH)_{2-x}$. Stoichiometric hydroxyapatite can have a chemical formula of $Ca_{10}(PO_4)_6(OH)_2$ or can be also written as $Ca_5(PO_4)_3(OH)$. Hydroxyapatite can be predominantly crystalline but may be present in amorphous forms.

The mineral coating, as described herein, can include at least about 1% hydroxyapatite. For example, the mineral coating can include at least about 1% hydroxyapatite; at least about 2% hydroxyapatite; at least about 3% hydroxyapatite; at least about 4% hydroxyapatite; at least about 5% hydroxyapatite; at least about 6% hydroxyapatite; at least about 7% hydroxyapatite; at least about 8% hydroxyapatite; at least about 9% hydroxyapatite; at least about 10% hydroxyapatite; at least about 11% hydroxyapatite; at least about 12% hydroxyapatite; at least about 13% hydroxyapatite; at least about 14% hydroxyapatite; at least about 15% hydroxyapatite; at least about 16% hydroxyapatite; at least about 17% hydroxyapatite; at least about 18% hydroxyapatite; at least about 19% hydroxyapatite; at least about 20% hydroxyapatite; at least about 21% hydroxyapatite; at least about 22% hydroxyapatite; at least about 23% hydroxyapatite; at least about 24% hydroxyapatite; at least about 25% hydroxyapatite; at least about 26% hydroxyapatite; at least about 27% hydroxyapatite; at least about 28% hydroxyapatite; at least about 29% hydroxyapatite; at least about 30% hydroxyapatite; at least about 31% hydroxyapatite; at least about 32% hydroxyapatite; at least about 33% hydroxyapatite; at least about 34% hydroxyapatite; at least about 35% hydroxyapatite; at least about 36% hydroxyapatite; at least about 37% hydroxyapatite; at least about 38% hydroxyapatite; at least about 39% hydroxyapatite; at least about 40% hydroxyapatite; at least about 41% hydroxyapatite; at least about 42% hydroxyapatite; at least about 43% hydroxyapatite; at least about 44% hydroxyapatite; at least about 45% hydroxyapatite; at least about 46% hydroxyapatite; at least about 47% hydroxyapatite; at least about 48% hydroxyapatite; at least about 49% hydroxyapatite; at least about 50% hydroxyapatite; at least about 51% hydroxyapatite; at least about 52% hydroxyapatite; at least about 53% hydroxyapatite; at least about 54% hydroxyapatite; at least about 55% hydroxyapatite; at least about 56% hydroxyapatite; at least about 57% hydroxyapatite; at least about 58% hydroxyapatite; at least about 59% hydroxyapatite; at least about 60% hydroxyapatite; at least about 61% hydroxyapatite; at least about 62% hydroxyapatite; at least about 63% hydroxyapatite; at least about 64% hydroxyapatite; at least about 65% hydroxyapatite; at least about 66% hydroxyapatite; at least about 67% hydroxyapatite; at least about 68% hydroxyapatite; at least about 69% hydroxyapatite; at least about 70% hydroxyapatite; at least about 71% hydroxyapatite; at least about 72% hydroxyapatite; at least about 73% hydroxyapatite; at least about 74% hydroxyapatite; at least about 75% hydroxyapatite; at least about 76% hydroxyapatite; at least about 77% hydroxyapatite; at least about 78% hydroxyapatite; at least about 79% hydroxyapatite; at least about 80% hydroxyapatite; at least about 81% hydroxyapatite; at least about 82% hydroxyapatite; at least about 83% hydroxyapatite; at least about 84% hydroxyapatite; at least about 85% hydroxyapatite; at least about 86% hydroxyapatite; at least about 87% hydroxyapatite; at least about 88% hydroxyapatite; at least about 89% hydroxyapatite; at least about 90% hydroxyapatite; at least about 91% hydroxyapatite; at least about 92% hydroxyapatite; at least about 93% hydroxyapatite; at least about 94% hydroxyapatite; at least about 95% hydroxyapatite; at least about 96% hydroxyapatite; at least about 97% hydroxyapatite; at least about 98% hydroxyapatite; at least about 99% hydroxyapatite; or at least about 100% hydroxyapatite. It is understood that recitation of the above discrete values includes a range between each recited value.

As another example, the mineral coating can include about 1% hydroxyapatite; about 2% hydroxyapatite; about 3% hydroxyapatite; about 4% hydroxyapatite; about 5% hydroxyapatite; about 6% hydroxyapatite; about 7% hydroxyapatite; about 8% hydroxyapatite; about 9% hydroxyapatite; about 10% hydroxyapatite; about 11% hydroxyapatite; about 12% hydroxyapatite; about 13% hydroxyapatite; about 14% hydroxyapatite; about 15% hydroxyapatite; about 16% hydroxyapatite; about 17% hydroxyapatite; about 18% hydroxyapatite; about 19% hydroxyapatite; about 20% hydroxyapatite; about 21% hydroxyapatite; about 22% hydroxyapatite; about 23% hydroxyapatite; about 24% hydroxyapatite; about 25% hydroxyapatite; about 26% hydroxyapatite; about 27% hydroxyapatite; about 28% hydroxyapatite; about 29% hydroxyapatite; about 30% hydroxyapatite; about 31% hydroxyapatite; about 32% hydroxyapatite; about 33% hydroxyapatite; about 34% hydroxyapatite; about 35% hydroxyapatite; about 36% hydroxyapatite; about 37% hydroxyapatite; about 38% hydroxyapatite; about 39% hydroxyapatite; about 40% hydroxyapatite; about 41% hydroxyapatite; about 42% hydroxyapatite; about 43% hydroxyapatite; about 44% hydroxyapatite; about 45% hydroxyapatite; about 46% hydroxyapatite; about 47% hydroxyapatite; about 48% hydroxyapatite; about 49% hydroxyapatite; about 50% hydroxyapatite; about 51% hydroxyapatite; about 52% hydroxyapatite; about 53% hydroxyapatite; about 54% hydroxyapatite; about 55% hydroxyapatite; about 56% hydroxyapatite; about 57% hydroxyapatite; about 58% hydroxyapatite; about 59% hydroxyapatite; about 60% hydroxyapatite; about 61% hydroxyapatite; about 62% hydroxyapatite; about 63% hydroxyapatite; about 64% hydroxyapatite; about 65% hydroxyapatite; about 66% hydroxyapatite; about 67% hydroxyapatite; about 68% hydroxyapatite; about 69% hydroxyapatite; about 70% hydroxyapatite; about 71% hydroxyapatite; about 72% hydroxyapatite; about 73% hydroxyapatite; about 74% hydroxyapatite; about 75% hydroxyapatite; about 76% hydroxyapatite; about 77% hydroxyapatite; about 78% hydroxyapatite; about 79% hydroxyapatite; about 80% hydroxyapatite; about 81% hydroxyapatite; about 82% hydroxyapatite; about 83% hydroxyapatite; about 84% hydroxyapatite; about 85% hydroxyapatite; about 86% hydroxyapatite; about 87% hydroxyapatite; about 88% hydroxyapatite; about 89% hydroxyapatite; about 90% hydroxyapatite; about 91% hydroxyapatite; about 92% hydroxyapatite; about 93% hydroxyapatite; about 94% hydroxyapatite; about 95% hydroxyapatite; about 96% hydroxyapatite; about 97% hydroxyapatite; about 98% hydroxyapatite; about 99% hydroxyapatite; or about 100% hydroxyapatite. It is understood that recitation of the above discrete values includes a range between each recited value.

The mineral coating, as described herein, can include octacalcium phosphate. Octacalcium phosphate has a chemical formula of Ca8H2(PO4)6.5H2O or can also be written as Ca4HO12P3. Octacalcium phosphate has been shown to be a precursor of hydroxyapatite. Hydrolysis of Octacalcium phosphate can create hydroxyapatite. Octacalcium phosphate can be predominantly crystalline but may be present in amorphous forms.

The mineral coating, as described herein, can include at least about 1% octacalcium phosphate. For example, the mineral coating can include at least about 1% octacalcium phosphate; at least about 2% octacalcium phosphate; at least about 3% octacalcium phosphate; at least about 4% octacalcium phosphate; at least about 5% octacalcium phosphate; at least about 6% octacalcium phosphate; at least about 7% octacalcium phosphate; at least about 8% octacalcium phosphate; at least about 9% octacalcium phosphate; at least about 10% octacalcium phosphate; at least about 11% octacalcium phosphate; at least about 12% octacalcium phosphate; at least about 13% octacalcium phosphate; at least about 14% octacalcium phosphate; at least about 15% octacalcium phosphate; at least about 16% octacalcium phosphate; at least about 17% octacalcium phosphate; at least about 18% octacalcium phosphate; at least about 19% octacalcium phosphate; at least about 20% octacalcium phosphate; at least about 21% octacalcium phosphate; at least about 22% octacalcium phosphate; at least about 23% octacalcium phosphate; at least about 24% octacalcium phosphate; at least about 25% octacalcium phosphate; at least about 26% octacalcium phosphate; at least about 27% octacalcium phosphate; at least about 28% octacalcium phosphate; at least about 29% octacalcium phosphate; at least about 30% octacalcium phosphate; at least about 31% octacalcium phosphate; at least about 32% octacalcium phosphate; at least about 33% octacalcium phosphate; at least about 34% octacalcium phosphate; at least about 35% octacalcium phosphate; at least about 36% octacalcium phosphate; at least about 37% octacalcium phosphate; at least about 38% octacalcium phosphate; at least about 39% octacalcium phosphate; at least about 40% octacalcium phosphate; at least about 41% octacalcium phosphate; at least about 42% octacalcium phosphate; at least about 43% octacalcium phosphate; at least about 44% octacalcium phosphate; at least about 45% octacalcium phosphate; at least about 46% octacalcium phosphate; at least about 47% octacalcium phosphate; at least about 48% octacalcium phosphate; at least about 49% octacalcium phosphate; at least about 50% octacalcium phosphate; at least about 51% octacalcium phosphate; at least about 52% octacalcium phosphate; at least about 53% octacalcium phosphate; at least about 54% octacalcium phosphate; at least about 55% octacalcium phosphate; at least about 56% octacalcium phosphate; at least about 57% octacalcium phosphate; at least about 58% octacalcium phosphate; at least about 59% octacalcium phosphate; at least about 60% octacalcium phosphate; at least about 61% octacalcium phosphate; at least about 62% octacalcium phosphate; at least about 63% octacalcium phosphate; at least about 64% octacalcium phosphate; at least about 65% octacalcium phosphate; at least about 66% octacalcium phosphate; at least about 67% octacalcium phosphate; at least about 68% octacalcium phosphate; at least about 69% octacalcium phosphate; at least about 70% octacalcium phosphate; at least about 71% octacalcium phosphate; at least about 72% octacalcium phosphate; at least about 73% octacalcium phosphate; at least about 74% octacalcium phosphate; at least about 75% octacalcium phosphate; at least about 76% octacalcium phosphate; at least about 77% octacalcium phosphate; at least about 78% octacalcium phosphate; at least about 79% octacalcium phosphate; at least about 80% octacalcium phosphate; at least about 81% octacalcium phosphate; at least about 82% octacalcium phosphate; at least about 83% octacalcium phosphate; at least about 84% octacalcium phosphate; at least about 85% octacalcium phosphate; at least about 86% octacalcium phosphate; at least about 87% octacalcium phosphate; at least about 88% octacalcium phosphate; at least about 89% octacalcium phosphate; at least about 90% octacalcium phosphate; at least about 91% octacalcium phosphate; at least about 92% octacalcium phosphate; at least about 93% octacalcium phosphate; at least about 94% octacalcium phosphate; at least about 95% octacalcium phosphate; at least about 96% octacalcium phosphate; at least about 97% octacalcium phosphate; at least about 98% octacalcium phosphate; at least about 99% octacalcium phosphate; or at least about 100% octacalcium phosphate. It is understood that recitation of the above discrete values includes a range between each recited value.

As another example, the mineral coating can include about 1% octacalcium phosphate; about 2% octacalcium phosphate; about 3% octacalcium phosphate; about 4% octacalcium phosphate; about 5% octacalcium phosphate; about 6% octacalcium phosphate; about 7% octacalcium phosphate; about 8% octacalcium phosphate; about 9% octacalcium phosphate; about 10% octacalcium phosphate; about 11% octacalcium phosphate; about 12% octacalcium phosphate; about 13% octacalcium phosphate; about 14% octacalcium phosphate; about 15% octacalcium phosphate; about 16% octacalcium phosphate; about 17% octacalcium phosphate; about 18% octacalcium phosphate; about 19% octacalcium phosphate; about 20% octacalcium phosphate; about 21% octacalcium phosphate; about 22% octacalcium phosphate; about 23% octacalcium phosphate; about 24% octacalcium phosphate; about 25% octacalcium phosphate; about 26% octacalcium phosphate; about 27% octacalcium phosphate; about 28% octacalcium phosphate; about 29% octacalcium phosphate; about 30% octacalcium phosphate; about 31% octacalcium phosphate; about 32% octacalcium phosphate; about 33% octacalcium phosphate; about 34% octacalcium phosphate; about 35% octacalcium phosphate; about 36% octacalcium phosphate; about 37% octacalcium phosphate; about 38% octacalcium phosphate; about 39% octacalcium phosphate; about 40% octacalcium phosphate; about 41% octacalcium phosphate; about 42% octacalcium phosphate; about 43% octacalcium phosphate; about 44% octacalcium phosphate; about 45% octacalcium phosphate; about 46% octacalcium phosphate; about 47% octacalcium phosphate; about 48% octacalcium phosphate; about 49% octacalcium phosphate; about 50% octacalcium phosphate; about 51% octacalcium phosphate; about 52% octacalcium phosphate; about 53% octacalcium phosphate; about 54% octacalcium phosphate; about 55% octacalcium phosphate; about 56% octacalcium phosphate; about 57% octacalcium phosphate; about 58% octacalcium phosphate; about 59% octacalcium phosphate; about 60% octacalcium phosphate; about 61% octacalcium phosphate; about 62% octacalcium phosphate; about 63% octacalcium phosphate; about 64% octacalcium phosphate; about 65% octacalcium phosphate; about 66% octacalcium phosphate; about 67% octacalcium phosphate; about 68% octacalcium phosphate; about 69% octacalcium phosphate; about 70% octacalcium phosphate; about 71% octacalcium phosphate; about 72% octacalcium phosphate; about 73% octacalcium phosphate; about 74% octacalcium phosphate; about 75% octacalcium phosphate; about 76% octacalcium phosphate; about 77% octacalcium phosphate; about 78% octacalcium phosphate; about 79% octacalcium phosphate; about 80% octacalcium phosphate; about 81% octacalcium phosphate; about 82% octacalcium phosphate; about 83% octacalcium phosphate; about 84% octacalcium phosphate; about 85% octacalcium phosphate; about 86% octacalcium phosphate; about 87% octacalcium phosphate; about 88% octacalcium phosphate; about 89% octacalcium phosphate; about 90% octacalcium phosphate; about 91% octacalcium phosphate; about 92% octacalcium phosphate; about 93% octacalcium phosphate; about 94% octacalcium phosphate; about 95% octacalcium phosphate; about 96% octacalcium phosphate; about 97% octacalcium phosphate; about 98% octacalcium phosphate; about 99% octacalcium phosphate; or about 100% octacalcium phosphate. It is understood that recitation of the above discrete values includes a range between each recited value.

The mineral coating, as described herein, can include at least about 1% porosity. For example, the mineral coating, as described herein, can include a porosity of at least about 1% porosity; at least about 2% porosity; at least about 3% porosity; at least about 4% porosity; at least about 5% porosity; at least about 6% porosity; at least about 7% porosity; at least about 8% porosity; at least about 9% porosity; at least about 10% porosity; at least about 11% porosity; at least about 12% porosity; at least about 13% porosity; at least about 14% porosity; at least about 15% porosity; at least about 16% porosity; at least about 17% porosity; at least about 18% porosity; at least about 19% porosity; at least about 20% porosity; at least about 21% porosity; at least about 22% porosity; at least about 23% porosity; at least about 24% porosity; at least about 25% porosity; at least about 26% porosity; at least about 27% porosity; at least about 28% porosity; at least about 29% porosity; at least about 30% porosity; at least about 31% porosity; at least about 32% porosity; at least about 33% porosity; at least about 34% porosity; at least about 35% porosity; at least about 36% porosity; at least about 37% porosity; at least about 38% porosity; at least about 39% porosity; at least about 40% porosity; at least about 41% porosity; at least about 42% porosity; at least about 43% porosity; at least about 44% porosity; at least about 45% porosity; at least about 46% porosity; at least about 47% porosity; at least about 48% porosity; at least about 49% porosity; at least about 50% porosity; at least about 51% porosity; at least about 52% porosity; at least about 53% porosity; at least about 54% porosity; at least about 55% porosity; at least about 56% porosity; at least about 57% porosity; at least about 58% porosity; at least about 59% porosity; at least about 60% porosity; at least about 61% porosity; at least about 62% porosity; at least about 63% porosity; at least about 64% porosity; at least about 65% porosity; at least about 66% porosity; at least about 67% porosity; at least about 68% porosity; at least about 69% porosity; at least about 70% porosity; at least about 71% porosity; at least about 72% porosity; at least about 73% porosity; at least about 74% porosity; at least about 75% porosity; at least about 76% porosity; at least about 77% porosity; at least about 78% porosity; at least about 79% porosity; at least about 80% porosity; at least about 81% porosity; at least about 82% porosity; at least about 83% porosity; at least about 84% porosity; at least about 85% porosity; at least about 86% porosity; at least about 87% porosity; at least about 88% porosity; at least about 89% porosity; at least about 90% porosity; at least about 91% porosity; at least about 92% porosity; at least about 93% porosity; at least about 94% porosity; at least about 95% porosity; at least about 96% porosity; at least about 97% porosity; at least about 98% porosity; at least about 99% porosity; or at least about 100% porosity. It is understood that recitation of the above discrete values includes a range between each recited value.

As another example, the mineral coating can include about 1% porosity; about 2% porosity; about 3% porosity; about 4% porosity; about 5% porosity; about 6% porosity; about 7% porosity; about 8% porosity; about 9% porosity; about 10% porosity; about 11% porosity; about 12% porosity; about 13% porosity; about 14% porosity; about 15% porosity; about 16% porosity; about 17% porosity; about 18% porosity; about 19% porosity; about 20% porosity; about 21% porosity; about 22% porosity; about 23% porosity; about 24% porosity; about 25% porosity; about 26% porosity; about 27% porosity; about 28% porosity; about 29% porosity; about 30% porosity; about 31% porosity; about 32% porosity; about 33% porosity; about 34% porosity; about 35% porosity; about 36% porosity; about 37% porosity; about 38% porosity; about 39% porosity; about 40% porosity; about 41% porosity; about 42% porosity; about 43% porosity; about 44% porosity; about 45% porosity; about 46% porosity; about 47% porosity; about 48% porosity; about 49% porosity; about 50% porosity; about 51% porosity; about 52% porosity; about 53% porosity; about 54% porosity; about 55% porosity; about 56% porosity; about 57% porosity; about 58% porosity; about 59% porosity; about 60% porosity; about 61% porosity; about 62% porosity; about 63% porosity; about 64% porosity; about 65% porosity; about 66% porosity; about 67% porosity; about 68% porosity; about 69% porosity; about 70% porosity; about 71% porosity; about 72% porosity; about 73% porosity; about 74% porosity; about 75% porosity; about 76% porosity; about 77% porosity; about 78% porosity; about 79% porosity; about 80% porosity; about 81% porosity; about 82% porosity; about 83% porosity; about 84% porosity; about 85% porosity; about 86% porosity; about 87% porosity; about 88% porosity; about 89% porosity; about 90% porosity; about 91% porosity; about 92% porosity; about 93% porosity; about 94% porosity; about 95% porosity; about 96% porosity; about 97% porosity; about 98% porosity; about 99% porosity; or about 100% porosity. It is understood that recitation of the above discrete values includes a range between each recited value.

The mineral coating, as described herein, can include a pore diameter between about 1 nm and about 3500 nm. As another example, the mineral coating, as described herein, can include a pore diameter between about 100 and about 350 nm. As another example, the mineral coating, as described herein, can include at least about 1 nm pore diameter; at least about 10 nm pore diameter; at least about 15 nm pore diameter; at least about 20 nm pore diameter; at least about 25 nm pore diameter; at least about 30 nm pore diameter; at least about 35 nm pore diameter; at least about 40 nm pore diameter; at least about 45 nm pore diameter; at least about 50 nm pore diameter; at least about 55 nm pore diameter; at least about 60 nm pore diameter; at least about 65 nm pore diameter; at least about 70 nm pore diameter; at least about 75 nm pore diameter; at least about 80 nm pore diameter; at least about 85 nm pore diameter; at least about 90 nm pore diameter; at least about 95 nm pore diameter; at least about 100 nm pore diameter; at least about 105 nm pore diameter; at least about 110 nm pore diameter; at least about 115 nm pore diameter; at least about 120 nm pore diameter; at least about 125 nm pore diameter; at least about 130 nm pore diameter; at least about 135 nm pore diameter; at least about 140 nm pore diameter; at least about 145 nm pore diameter; at least about 150 nm pore diameter; at least about 155 nm pore diameter; at least about 160 nm pore diameter; at least about 165 nm pore diameter; at least about 170 nm pore diameter; at least about 175 nm pore diameter; at least about 180 nm pore diameter; at least about 185 nm pore diameter; at least about 190 nm pore diameter; at least about 195 nm pore diameter; at least about 200 nm pore diameter; at least about 205 nm pore diameter; at least about 210 nm pore diameter; at least about 215 nm pore diameter; at least about 220 nm pore diameter; at least about 225 nm pore diameter; at least about 230 nm pore diameter; at least about 235 nm pore diameter; at least about 240 nm pore diameter; at least about 245 nm pore diameter; at least about 250 nm pore diameter; at least about 255 nm pore diameter; at least about 260 nm pore diameter; at least about 265 nm pore diameter; at least about 270 nm pore diameter; at least about 275 nm pore diameter; at least about 280 nm pore diameter; at least about 285 nm pore diameter; at least about 290 nm pore diameter; at least about 295 nm pore diameter; at least about 300 nm pore diameter; at least about 305 nm pore diameter; at least about 310 nm pore diameter; at least about 315 nm pore diameter; at least about 320 nm pore diameter; at least about 325 nm pore diameter; at least about 330 nm pore diameter; at least about 335 nm pore diameter; at least about 340 nm pore diameter; at least about 345 nm pore diameter; at least about 350 nm pore diameter; at least about 355 nm pore diameter; at least about 360 nm pore diameter; at least about 365 nm pore diameter; at least about 370 nm pore diameter; at least about 375 nm pore diameter; at least about 400 nm pore diameter; at least about 410 nm pore diameter; at least about 420 nm pore diameter; at least about 430 nm pore diameter; at least about 440 nm pore diameter; at least about 450 nm pore diameter; at least about 460 nm pore diameter; at least about 470 nm pore diameter; at least about 480 nm pore diameter; at least about 490 nm pore diameter; at least about 500 nm pore diameter; at least about 600 nm pore diameter; at least about 700 nm pore diameter; at least about 800 nm pore diameter; at least about 900 nm pore diameter; at least about 1000 nm pore diameter; at least about 1100 nm pore diameter; at least about 1200 nm pore diameter; at least about 1300 nm pore diameter; at least about 1400 nm pore diameter; at least about 1500 nm pore diameter; at least about 1600 nm pore diameter; at least about 1700 nm pore diameter; at least about 1800 nm pore diameter; at least about 1900 nm pore diameter; at least about 2000 nm pore diameter; at least about 2100 nm pore diameter; at least about 2200 nm pore diameter; at least about 2300 nm pore diameter; at least about 2400 nm pore diameter; at least about 2500 nm pore diameter; at least about 2600 nm pore diameter; at least about 2700 nm pore diameter; at least about 2800 nm pore diameter; at least about 2900 nm pore diameter; at least about 3000 nm pore diameter; at least about 3100 nm pore diameter; at least about 3200 nm pore diameter; at least about 3300 nm pore diameter; at least about 3400 nm pore diameter; or at least about 3500 nm pore diameter. It is understood that recitation of the above discrete values includes a range between each recited value.

As another example, the mineral coating, as described herein, can include about 1 nm pore diameter; about 10 nm pore diameter; about 20 nm pore diameter; about 30 nm pore diameter; about 40 nm pore diameter; about 50 nm pore diameter; about 55 nm pore diameter; about 60 nm pore diameter; about 65 nm pore diameter; about 70 nm pore diameter; about 75 nm pore diameter; about 80 nm pore diameter; about 85 nm pore diameter; about 90 nm pore diameter; about 95 nm pore diameter; about 100 nm pore diameter; about 105 nm pore diameter; about 110 nm pore diameter; about 115 nm pore diameter; about 120 nm pore diameter; about 125 nm pore diameter; about 130 nm pore diameter; about 135 nm pore diameter; about 140 nm pore diameter; about 145 nm pore diameter; about 150 nm pore diameter; about 155 nm pore diameter; about 160 nm pore diameter; about 165 nm pore diameter; about 170 nm pore diameter; about 175 nm pore diameter; about 180 nm pore diameter; about 185 nm pore diameter; about 190 nm pore diameter; about 195 nm pore diameter; about 200 nm pore diameter; about 205 nm pore diameter; about 210 nm pore diameter; about 215 nm pore diameter; about 220 nm pore diameter; about 225 nm pore diameter; about 230 nm pore diameter; about 235 nm pore diameter; about 240 nm pore diameter; about 245 nm pore diameter; about 250 nm pore diameter; about 255 nm pore diameter; about 260 nm pore diameter; about 265 nm pore diameter; about 270 nm pore diameter; about 275 nm pore diameter; about 280 nm pore diameter; about 285 nm pore diameter; about 290 nm pore diameter; about 295 nm pore diameter; about 300 nm pore diameter; about 305 nm pore diameter; about 310 nm pore diameter; about 315 nm pore diameter; about 320 nm pore diameter; about 320 nm pore diameter; about 330 nm pore diameter; about 335 nm pore diameter; about 340 nm pore diameter; about 345 nm pore diameter; about 350 nm pore diameter; about 355 nm pore diameter; about 360 nm pore diameter; about 365 nm pore diameter; about 370 nm pore diameter; about 375 nm pore diameter; about 380 nm pore diameter; about 390 nm pore diameter; about 400 nm pore diameter; about 410 nm pore diameter; about 420 nm pore diameter; about 430 nm pore diameter; about 440 nm pore diameter; about 450 nm pore diameter; about 460 nm pore diameter; about 470 nm pore diameter; about 480 nm pore diameter; about 490 nm pore diameter; about 500 nm pore diameter; about 600 nm pore diameter; about 700 nm pore diameter; about 800 nm pore diameter; about 900 nm pore diameter; about 1000 nm pore diameter; about 1100 nm pore diameter; about 1200 nm pore diameter; about 1300 nm pore diameter; about 1400 nm pore diameter; about 1500 nm pore diameter; about 1600 nm pore diameter; about 1700 nm pore diameter; about 1800 nm pore diameter; about 1900 nm pore diameter; about 2000 nm pore diameter; about 2100 nm pore diameter; about 2200 nm pore diameter; about 2300 nm pore diameter; about 2400 nm pore diameter; about 2500 nm pore diameter; about 2600 nm pore diameter; about 2700 nm pore diameter; about 2800 nm pore diameter; about 2900 nm pore diameter; about 3000 nm pore diameter; about 3100 nm pore diameter; about 3200 nm pore diameter; about 3300 nm pore diameter; about 3400 nm pore diameter; or about 3500 nm pore diameter. It is understood that recitation of the above discrete values includes a range between each recited value.

The mineral coating, as described herein, can include a ratio of at least about 0.1 Ca/P. For example, the mineral coating can include a ratio of at least about 0.1 Ca/P; at least about 0.2 Ca/P; at least about 0.3 Ca/P; at least about 0.4 Ca/P; at least about 0.5 Ca/P; at least about 0.6 Ca/P; at least about 0.7 Ca/P; at least about 0.8 Ca/P; at least about 0.9 Ca/P; at least about 1.0 Ca/P; at least about 1.1 Ca/P; at least about 1.2 Ca/P; at least about 1.3 Ca/P; at least about 1.4 Ca/P; at least about 1.5 Ca/P; at least about 1.6 Ca/P; at least about 1.7 Ca/P; at least about 1.8 Ca/P; at least about 1.9 Ca/P; at least about 2.0 Ca/P; at least about 2.1 Ca/P; at least about 2.2 Ca/P; at least about 2.3 Ca/P; at least about 2.4 Ca/P; at least about 2.5 Ca/P; at least about 2.6 Ca/P; at least about 2.7 Ca/P; at least about 2.8 Ca/P; at least about 2.9 Ca/P; at least about 3.0 Ca/P; at least about 3.1 Ca/P; at least about 3.2 Ca/P; at least about 3.3 Ca/P; at least about 3.4 Ca/P; at least about 3.5 Ca/P; at least about 3.6 Ca/P; at least about 3.7 Ca/P; at least about 3.8 Ca/P; at least about 3.9 Ca/P; at least about 4 Ca/P; at least about 5 Ca/P; at least about 6 Ca/P; at least about 7 Ca/P; at least about 8 Ca/P; at least about 9 Ca/P; at least about 10 Ca/P; at least about 11 Ca/P; at least about 12 Ca/P; at least about 13 Ca/P; at least about 14 Ca/P; at least about 15 Ca/P; at least about 16 Ca/P; at least about 17 Ca/P; at least about 18 Ca/P; at least about 19 Ca/P; or at least about 20 Ca/P. It is understood that recitation of the above discrete values includes a range between each recited value.

As another example, the mineral coating can include a ratio of about 0.1 Ca/P, about 0.2 Ca/P, about 0.3 Ca/P, about 0.4 Ca/P, about 0.5 Ca/P, about 0.6 Ca/P, about 0.7 Ca/P, about 0.8 Ca/P, about 0.9 Ca/P, about 1.0 Ca/P, about 1.1 Ca/P, about 1.2 Ca/P, about 1.3 Ca/P, about 1.4 Ca/P, about 1.5 Ca/P, about 1.6 Ca/P, about 1.7 Ca/P, about 1.8 Ca/P, about 1.9 Ca/P, about 2.0 Ca/P, about 2.1 Ca/P, about 2.2 Ca/P, about 2.3 Ca/P, about 2.4 Ca/P, about 2.5 Ca/P, about 2.6 Ca/P, about 2.7 Ca/P, about 2.8 Ca/P, about 2.9 Ca/P, about 3.0 Ca/P, about 3.1 Ca/P, about 3.2 Ca/P, about 3.3 Ca/P, about 3.4 Ca/P, about 3.5 Ca/P, about 3.6 Ca/P, about 3.7 Ca/P, about 3.8 Ca/P, about 3.9 Ca/P, about 4 Ca/P, about 5 Ca/P, about 6 Ca/P, about 7 Ca/P, about 8 Ca/P, about 9 Ca/P, about 10 Ca/P, about 11 Ca/P, about 12 Ca/P, about 13 Ca/P, about 14 Ca/P, about 15 Ca/P, about 16 Ca/P, about 17 Ca/P, about 18 Ca/P, about 19 Ca/P, or about 20 Ca/P. It is understood that recitation of the above discrete values includes a range between each recited value.

A mineral coating, as described herein, can be characterized by conventional methods. For example, mineral formation in mSBF can be tracked by analyzing changes in solution calcium concentration using a calcium sensitive electrode (Denver Instrument, Denver, Colo.). After their growth, the mineral matrices can be dissolved and analyzed for calcium and phosphate ion content to quantify mineral formation, and the mineral crystals can be analyzed morphologically and compositionally using a scanning electron microscope (SEM), e.g., with a Noran SiLi detector for elemental analysis.

For example, the crystalline phase can be characterized by X-ray diffraction, where 2θ is in the range of 15-35° or 25.8°, 28.1°, 28.9°, 31.8°, or 32.1°.

As another example, as described herein, the chemical composition or crystalline phase can be characterized by Fourier transform infrared spectroscopy (FTIR), where carbonate peaks can be in the 1400-1500 cm-1 region and phosphate peaks can be in the 900-1100 cm-1 region or about 570 cm-1, 962 cm-1, or 1050 cm.

As another example, as described herein, dissolution of mineral layers can also be characterized by measuring release of calcium and phosphate ions during incubation in tris-buffered saline at physiologically relevant conditions (e.g., 37° C., pH 7.4).

As another example, as described herein, calcium and phosphate concentrations can be measured using previously described colorimetric assays (see Murphy et al., "Bioinspired growth of crystalline carbonate apatite on biodegradable polymer substrata". J Am Chem Soc 124:1910-7, 2002). Each of the characterization methods described herein are routine in analysis of inorganic materials and is consistent with FDA's good guidance practices for design and testing of calcium phosphate coatings (see Devices FDoGaR. Calcium phosphate coating draft guidance for preparation of FDA submissions for orthopedic and dental endosseous implants. 1997).

As another example, as described herein, the mineral coating, can be predominantly crystalline, but can be present in amorphous forms. For example, the mineral coating can have at least about 5% crystallinity. For example, a mineral coating can include at least about 5% crystallinity; at least about 10% crystallinity; at least about 15% crystallinity; at least about 20% crystallinity; at least about 25% crystallinity; at least about 30% crystallinity; at least about 35% crystallinity; at least about 40% crystallinity; at least about 45% crystallinity; at least about 46% crystallinity; at least about 47% crystallinity; at least about 48% crystallinity; at least about 49% crystallinity; at least about 50% crystallinity; at least about 51% crystallinity; at least about 52% crystallinity; at least about 53% crystallinity; at least about 54% crystallinity; at least about 55% crystallinity; at least about 56% crystallinity; at least about 57% crystallinity; at least about 58% crystallinity; at least about 59% crystallinity; at least about 60% crystallinity; at least about 61% crystallinity; at least about 62% crystallinity; at least about 63% crystallinity; at least about 64% crystallinity; at least about 65% crystallinity; at least about 66% crystallinity; at least about 67% crystallinity; at least about 68% crystallinity; at least about 69% crystallinity; at least about 70% crystallinity; at least about 71% crystallinity; at least about 72% crystallinity; at least about 73% crystallinity; at least about 74% crystallinity; at least about 75% crystallinity; at least about 76% crystallinity; at least about 77% crystallinity; at least about 78% crystallinity; at least about 79% crystallinity; at least about 80% crystallinity; at least about 81% crystallinity; at least about 82% crystallinity; at least about 83% crystallinity; at least about 84% crystallinity; at least about 85% crystallinity; at least about 86% crystallinity; at least about 87% crystallinity; at least about 88% crystallinity; at least about 89% crystallinity; at least about 90% crystallinity; at least about 91% crystallinity; at least about 92% crystallinity; at least about 93% crystallinity; at least about 94% crystallinity; at least about 95% crystallinity; at least about 96% crystallinity; at least about 97% crystallinity; at least about 98% crystallinity; at least about 99% crystallinity; or at least about 100% crystallinity. It is understood that recitation of the above discrete values includes a range between each recited value.

As another example, a mineral coating can include about 5% crystallinity; 10% crystallinity; about 15% crystallinity; about 20% crystallinity; about 25% crystallinity; about 30% crystallinity; about 35% crystallinity; about 40% crystallinity; about 45% crystallinity; about 46% crystallinity; about 47% crystallinity; about 48% crystallinity; about 49% crystallinity; about 50% crystallinity; about 51% crystallinity; about 52% crystallinity; about 53% crystallinity; about 54% crystallinity; about 55% crystallinity; about 56% crystallinity; about 57% crystallinity; about 58% crystallinity; about 59% crystallinity; about 60% crystallinity; about 61% crystallinity; about 62% crystallinity; about 63% crystallinity; about 64% crystallinity; about 65% crystallinity; about 66% crystallinity; about 67% crystallinity; about 68% crystallinity; about 69% crystallinity; about 70% crystallinity; about 71% crystallinity; about 72% crystallinity; about 73% crystallinity; about 74% crystallinity; about 75% crystallinity; about 76% crystallinity; about 77% crystallinity; about 78% crystallinity; about 79% crystallinity; about 80% crystallinity; about 81% crystallinity; about 82% crystallinity; about 83% crystallinity; about 84% crystallinity; about 85% crystallinity; about 86% crystallinity; about 87% crystallinity; about 88% crystallinity; about 89% crystallinity; about 90% crystallinity; about 91% crystallinity; about 92% crystallinity; about 93% crystallinity; about 94% crystallinity; about 95% crystallinity; about 96% crystallinity; about 97% crystallinity; about 98% crystallinity; about 99% crystallinity; or about 100% crystallinity. It is understood that recitation of the above discrete values includes a range between each recited value.

In some embodiments, the coated bone material is comprising, consisting essentially of, or consisting of a plurality of porous macroparticles lyophilized into a rectangular shape prepared from ceramic material and embedded in a matrix of collagen. The plurality of porous macroparticles are coated with a mineral coating. The mineral coating comprises, consists essentially of, or consists of a carbonated calcium-deficient hydroxyapatite component. The bone material also comprises a plurality of surface markers, for example, recesses, projections, or a combination thereof. In some embodiments, as illustrated in FIG. 8, the bone material includes one or more channels 316 (which are recesses) which not only serve as surface markers but also increase the surface area and hydration characteristics of the bone material. In some embodiments, channels are recesses that can have a macro half-cylindrical shape. In other embodiments, channels can have other shapes, for example, a trapezoidal or square shape, that can be easily identifiable under visible light. In some embodiments, hydration channel can have a 1 mm diameter.

In various embodiments, the plurality of lyophilized porous macroparticles may include, but are not limited to, MasterGraft® Strip produced by Medtronic Sofamor Danek, Inc., Memphis, Tenn.; MasterGraft® Putty produced by Medtronic Sofamor Danek, Inc., Memphis, Tenn., and Matrix EXT compression resistant products produced by Medtronic Sofamor Danek, Inc., Memphis, Tenn.

In other embodiments, the lyophilized porous macroparticles are coated with a mineral coating which comprises, consists essentially of, or consists of a plate-like nanostructure including a carbonate-substituted, calcium-deficient hydroxyapatite component. These mineral coatings are like bone and have been found to stimulate bone cells creating an enhanced cellular environment for bone healing. In these embodiments, the lyophilized porous macroparticles whether they are or are not coated can be formed into strips or other resorbable osteoconductive cohesive scaffolds. While easily discernable under scanning electron microscope (SEM), the strips or scaffolds coated with the mineral coating are not readily distinguished under visible light. In sum, to the naked eye, whether the strips are or are not coated, visually, they may appear identical. It has also been found unexpectedly that the surface markers used to texturize the coated macroparticles serve not only to differentiate between coated and uncoated grafts but also increase the surface area of the coated macroparticles, exhibit increasing hydration characteristics and enhanced mechanical characteristics of a resulting bone material allowing for improved biological integration into a selected surgical site. For example, while the surface area of a MasterGraft® granule is from about 0.3 to about 0.5 $m^2/g$, the surface area of a MasterGraft® granule coated with a mineral coating comprising nanoparticles having carbonate substituted, calcium-deficient hydroxyapatite including surface markers provides an increase in surface area of from about 300 to about 500% to a surface area of from about 2, 3, 4, 5 $m^2/g$. 6, 7, 8, 9, 10, 15, 20, 25, 30, 35, 40, 45, 50, 55, 60, 65, 70, 75, 80, 85, 90, 95 to about 100 $m^2/g$.

In various embodiments, the surface markers include, without limitation, macro texture features formed by applying texture patterns to one side of the bone material formed in the mold surface or by cutting and etching texture patterns on most surfaces of the bone material after lyophilization. These designs can be the macro structures in patterns of recesses and/or projections of a variety of shapes. In some embodiments, macro surface markers include a plurality of recesses, projections, or a combination thereof, for example, squared or curved surfaces and various types of engineered notches. In various embodiments, the recesses, projections, or combinations thereof form a pattern or random shapes. In some aspects, the recesses, projections or combinations thereof form square, cylindrical, corrugated, notched, curved, waffle, hexagonal or honeycomb or oval shapes in the mineral coated bone material. In other embodiments, the plurality of recesses, projections or combinations thereof are radiographic markers, hydration channels, or indicia to determine bone growth within or bone growth adjacent to the bone material. It will be understood that the surface markers can have an alternating pattern (e.g., circles alternating with squares, etc.) or can be disposed throughout the material randomly in a non-uniform pattern.

In various embodiments, bone implants prepared of uncoated MasterGraft®, for example, can contain micropores of about 500 μm. The addition of a mineral coating having micropores increases the surface area of MasterGraft® bone implant and enhances the dissolution rate of $Ca^{2+}$ and $PO_4^-$. As a result of the increase in the dissolution rate of $Ca^{2+}$ and $PO_4^-$ new mineral deposition of bone material increases. Further, micron-sized grains may be removed following cell-mediated resorption. In various embodiments, other kinds of bone material can be mineral coated with coatings having surface markers as described in this application.

In other embodiments, bone materials are coated with mineralized coatings having a plate-like nanostructure of carbonate substituted, calcium-deficient hydroxyapatite (HA/TCP) The resulting nanopore size varies from about 0.1 μm to about 0.2 μm. In these embodiments, the nano morphology of the mineral coating increases the specific surface are of the bone implant and as a result it stimulates bone cell growth. In addition, the increased surface area further enhances early-stage dissolution increasing the availability of $Ca^{2+}$ and $PO_4^-$, thus increasing new mineral deposition. In several aspects, the bone material has pores (i) from about 50 μm to about 500 μm for bone growth or (ii) from about 500 μm to about 5 mm for vascularization.

A modified simulated body fluid as described herein can be used to mineral coat a scaffold. For example, the scaffold can be immersed and incubated in a modified simulated body fluid. As another example, the modified simulated body fluid can be replaced, replenished, or removed and added at least about once a day; at least about twice per day; or at least about three times per day. As another example, the modified simulated body fluid can be replaced at least about once every day; at least about once every two days; at least once every three days; at least once every four days; at least once every five days; at least once every six days; or at least once every seven days.

As described herein, a modified simulated body fluid can be a solution of ionic constituents of blood plasma, with double the concentrations of calcium and phosphate ions.

As described herein, a modified simulated body fluid can be a solution comprising NaCl, KCl, MgCl2, MgSO4, NaHCO$_3$, CaCl2, and KH2PO4.

A modified simulated body fluid can include at least about 1 mM NaCl. For example, a modified simulated body fluid can include at least about 1 mM NaCl; at least about 10 mM NaCl; at least about 20 mM NaCl; at least about 30 mM NaCl; at least about 40 mM NaCl; at least about 50 mM NaCl; at least about 60 mM NaCl; at least about 70 mM NaCl; at least about 80 mM NaCl; at least about 90 mM NaCl; at least about 100 mM NaCl; at least about 110 mM NaCl; at least about 120 mM NaCl; at least about 130 mM NaCl; at least about 140 mM NaCl; at least about 150 mM NaCl; at least about 160 mM NaCl; at least about 170 mM NaCl; at least about 180 mM NaCl; at least about 190 mM NaCl; at least about 200 mM NaCl; at least about 300 mM NaCl; at least about 400 mM NaCl; at least about 500 mM NaCl; at least about 600 mM NaCl; at least about 700 mM NaCl; at least about 800 mM NaCl; at least about 900 mM NaCl; at least about 1000 mM NaCl; at least about 1100 mM NaCl; at least about 1200 mM NaCl; at least about 1300 mM NaCl; at least about 1400 mM NaCl; at least about 1500 mM NaCl; at least about 1600 mM NaCl; at least about 1700 mM NaCl; at least about 1800 mM NaCl; at least about 1900 mM NaCl; or at least about 2000 mM NaCl. It is understood that recitation of the above discrete values includes a range between each recited value.

As another example, a modified simulated body fluid can include about 1 mM NaCl, about 10 mM NaCl; about 20 mM NaCl; about 30 mM NaCl; about 40 mM NaCl; about 50 mM NaCl; about 60 mM NaCl; about 70 mM NaCl; about 80 mM NaCl; about 90 mM NaCl; about 100 mM NaCl; about 110 mM NaCl; about 120 mM NaCl; about 130 mM NaCl; about 140 mM NaCl; about 150 mM NaCl; about 160 mM NaCl; about 170 mM NaCl; about 180 mM NaCl; about 190 mM NaCl; about 200 mM NaCl; about 300 mM NaCl; about 400 mM NaCl; about 500 mM NaCl; about 600 mM NaCl; about 700 mM NaCl; about 800 mM NaCl; about 900 mM NaCl; about 1000 mM NaCl; about 1100 mM NaCl; about 1200 mM NaCl; about 1300 mM NaCl; about 1400 mM NaCl; about 1500 mM NaCl; about 1600 mM NaCl; about 1700 mM NaCl; about 1800 mM NaCl; about 1900 mM NaCl; or about 2000 mM NaCl. It is understood that recitation of the above discrete values includes a range between each recited value.

A modified simulated body fluid can include at least about 0.4 mM KCl. For example, a modified simulated body fluid can include at least about 0.4 mM KCl; at least about 1 mM KCl; at least about 2 mM KCl; at least about 3 mM KCl; at least about 4 mM KCl; at least about 5 mM KCl; at least about 6 mM KCl; at least about 7 mM KCl; at least about 8 mM KCl; at least about 9 mM KCl; at least about 10 mM KCl; at least about 11 mM KCl; at least about 12 mM KCl; at least about 13 mM KCl; at least about 14 mM KCl; at least about 15 mM KCl; at least about 16 mM KCl; at least about 17 mM KCl; at least about 18 mM KCl; at least about 19 mM KCl; at least about 20 mM KCl; at least about 21 mM KCl; at least about 22 mM KCl; at least about 23 mM KCl; at least about 24 mM KCl; at least about 25 mM KCl; at least about 26 mM KCl; at least about 27 mM KCl; at least about 28 mM KCl; at least about 29 mM KCl; at least about 30 mM KCl; at least about 31 mM KCl; at least about 32 mM KCl; at least about 33 mM KCl; at least about 34 mM KCl; at least about 35 mM KCl; at least about 36 mM KCl; at least about 37 mM KCl; at least about 38 mM KCl; at least about 39 mM KCl; at least about 40 mM KCl; at least about 41 mM KCl; at least about 42 mM KCl; at least about 43 mM KCl; at least about 44 mM KCl; at least about 45 mM KCl; at least about 46 mM KCl; at least about 47 mM KCl; at least about 48 mM KCl; at least about 49 mM KCl; at least about 50 mM KCl; at least about 51 mM KCl; at least about 52 mM KCl; at least about 53 mM KCl; at least about 54 mM KCl; at least about 55 mM KCl; at least about 56 mM KCl; at least about 57 mM KCl; at least about 58 mM KCl; at least about 59 mM KCl; at least about 60 mM KCl; at least about 61 mM KCl; at least about 62 mM KCl; at least about 63 mM KCl; at least about 64 mM KCl; at least about 65 mM KCl; at least about 66 mM KCl; at least about 67 mM KCl; at least about 68 mM KCl; at least about 69 mM KCl; at least about 70 mM KCl; at least about 71 mM KCl; at least about 72 mM KCl; at least about 73 mM KCl; at least about 74 mM KCl; at least about 75 mM KCl; at least about 76 mM KCl; at least about 77 mM KCl; at least about 78 mM KCl; at least about 79 mM KCl; or at least about 80 mM KCl. It is understood that recitation of the above discrete values includes a range between each recited value.

As another example, a modified simulated body fluid can include about 0.4 mM KCl, about 1 mM KCl, about 2 mM KCl, about 3 mM KCl, about 4 mM KCl, about 5 mM KCl, about 6 mM KCl, about 7 mM KCl, about 8 mM KCl, about 9 mM KCl, about 10 mM KCl, about 11 mM KCl, about 12 mM KCl, about 13 mM KCl, about 14 mM KCl, about 15 mM KCl, about 16 mM KCl, about 17 mM KCl, about 18 mM KCl, about 19 mM KCl, about 20 mM KCl, about 21 mM KCl, about 22 mM KCl, about 23 mM KCl, about 24 mM KCl, about 25 mM KCl, about 26 mM KCl, about 27 mM KCl, about 28 mM KCl, about 29 mM KCl, about 30 mM KCl, about 31 mM KCl, about 32 mM KCl, about 33 mM KCl, about 34 mM KCl, about 35 mM KCl, about 36 mM KCl, about 37 mM KCl, about 38 mM KCl, about 39 mM KCl, about 40 mM; about 41 mM KCl, about 42 mM KCl, about 43 mM KCl, about 44 mM KCl, about 45 mM KCl, about 46 mM KCl, about 47 mM KCl, about 48 mM KCl, about 49 mM KCl, about 50 mM KCl, about 51 mM KCl, about 52 mM KCl, about 53 mM KCl, about 54 mM KCl, about 55 mM KCl, about 56 mM KCl, about 57 mM KCl, about 58 mM KCl, about 59 mM KCl, about 60 mM KCl, about 61 mM KCl, about 62 mM KCl, about 63 mM KCl, about 64 mM KCl, about 65 mM KCl, about 66 mM KCl, about 67 mM KCl, about 68 mM KCl, about 69 mM KCl, about 70 mM KCl, about 71 mM KCl, about 72 mM KCl, about 73 mM KCl, about 74 mM KCl, about 75 mM KCl, about 76 mM KCl, about 77 mM KCl, about 78 mM KCl, about 79 mM KCl. or about 80 mM KCl. It is understood that recitation of the above discrete values includes a range between each recited value.

A modified simulated body fluid can include at least about 0.1 mM MgCl$_2$. For example, a modified simulated body fluid can include at least about 0.1 mM MgCl$_2$, at least about 0.25 mM MgCl$_2$, at least about 0.5 mM MgCl$_2$, at least about 1 mM MgCl$_2$, at least about 1.25 mM MgCl$_2$, at least about 1.5 mM MgCl$_2$, at least about 1.75 mM MgCl$_2$, at least about 2 mM MgCl$_2$, at least about 2.25 mM MgCl$_2$, at least about 2.5 mM MgCl$_2$, at least about 2.75 mM MgCl$_2$, at least about 3 mM MgCl$_2$, at least about 3.25 mM MgCl$_2$, at least about 3.5 mM MgCl$_2$, at least about 3.75 mM MgCl$_2$, at least about 4 mM MgCl$_2$, at least about 4.25 mM MgCl$_2$, at least about 4.5 mM MgCl$_2$, at least about 4.75 mM MgCl$_2$, at least about 5 mM MgCl$_2$, at least about 5.25 mM MgCl$_2$, at least about 5.5 mM MgCl$_2$, at least about 5.75 mM MgCl$_2$, at least about 6 mM MgCl$_2$, at least about 6.25 mM MgCl$_2$, at least about 6.5 mM MgCl$_2$, at least about 6.75 mM MgCl$_2$, at least about 7 mM MgCl$_2$, at least about 7.25 mM MgCl$_2$, at least about 7.5 mM MgCl$_2$, at least about 7.75 mM MgCl$_2$, at least about 8 mM MgCl$_2$, at least about 8.25 mM MgCl$_2$, at least about 8.5 mM MgCl$_2$, at least about 8.75 mM MgCl$_2$, at least about 9 mM MgCl$_2$, at least about 9.25 mM MgCl$_2$, at least about 9.5 mM MgCl$_2$, at least about 9.75 mM MgCl$_2$, at least about 10 mM MgCl$_2$, at least about 11 mM MgCl$_2$, at least about 12 mM MgCl$_2$, at least about 13 mM MgCl$_2$, at least about 14 mM MgCl$_2$, at least about 15 mM MgCl$_2$, at least about 16 mM MgCl$_2$, at least about 17 mM MgCl$_2$, at least about 18 mM MgCl$_2$, at least about 19 mM MgCl$_2$, at least about 20 mM MgCl$_2$, at least about 21 mM MgCl$_2$, at least about 22 mM MgCl$_2$, at least about 23 mM MgCl$_2$, at least about 24 mM MgCl$_2$, at least about 25 mM MgCl$_2$, at least about 26 mM MgCl$_2$, at least about 27 mM MgCl$_2$, at least about 28 mM MgCl$_2$, at least about 29 mM MgCl$_2$, at least about 30 mM MgCl$_2$, at least about 31 mM MgCl$_2$, at least about 32 mM MgCl$_2$, at least about 33 mM MgCl$_2$, at least about 34 mM MgCl$_2$, at least about 35 mM MgCl$_2$, at least about 36 mM MgCl$_2$, at least about 37 mM MgCl$_2$, at least about 38 mM MgCl$_2$, at least about 39 mM MgCl$_2$, at least about 40 mM MgCl$_2$, at least about 41 mM MgCl$_2$, at least about 42 mM MgCl$_2$, at least about 43 mM MgCl$_2$, at least about 44 mM MgCl$_2$, at least about 45 mM MgCl$_2$, at least about 46 mM MgCl$_2$, at least about 47 mM MgCl$_2$, at least about 48 mM MgCl$_2$, at least about 49 mM MgCl$_2$, or at least about 50 mM MgCl$_2$. It is understood that recitation of the above discrete values includes a range between each recited value.

As another example, a modified simulated body fluid can include about 0.1 mM MgCl$_2$, at least about 0.25 mM MgCl$_2$, about 0.5 mM MgCl$_2$, about 1 mM MgCl$_2$, about 1.25 mM MgCl$_2$, about 1.5 mM MgCl$_2$, about 1.75 mM MgCl$_2$, about 2 mM MgCl$_2$, about 2.25 mM MgCl$_2$, about 2.5 mM MgCl$_2$, about 2.75 mM MgCl$_2$, about 3 mM MgCl$_2$, about 3.25 mM MgCl$_2$, about 3.5 mM MgCl$_2$, about 3.75 mM MgCl$_2$, about 4 mM MgCl$_2$, about 4.25 mM MgCl$_2$, about 4.5 mM MgCl$_2$, about 4.75 mM MgCl$_2$, about 5 mM MgCl$_2$, about 5.25 mM MgCl$_2$, about 5.5 mM MgCl$_2$, about 5.75 mM MgCl$_2$, about 6 mM MgCl$_2$, about 6.25 mM MgCl$_2$, about 6.5 mM MgCl$_2$, about 6.75 mM MgCl$_2$, about 7 mM MgCl$_2$, about 7.25 mM MgCl$_2$, about 7.5 mM MgCl$_2$, about 7.75 mM MgCl$_2$, about 8 mM MgCl$_2$, about 8.25 mM MgCl$_2$, about 8.5 mM MgCl$_2$, about 8.75 mM MgCl$_2$, about 9 mM MgCl$_2$, about 9.25 mM MgCl$_2$, about 9.5 mM MgCl$_2$, about 9.75 mM MgCl$_2$, about 10 mM MgCl$_2$, about 11 mM MgCl$_2$, about 12 mM MgCl$_2$, about 13 mM MgCl$_2$, about 14 mM MgCl$_2$, about 15 mM MgCl$_2$, about 16 mM MgCl$_2$, about 17 mM MgCl$_2$, about 18 mM MgCl$_2$, about 19 mM MgCl$_2$, about 20 mM MgCl$_2$, about 21 mM MgCl$_2$, about 22 mM MgCl$_2$, about 23 mM MgCl$_2$, about 24 mM MgCl$_2$, about 25 mM MgCl$_2$, about 26 mM MgCl$_2$, about 27 mM MgCl$_2$, about 28 mM MgCl$_2$, about 29 mM MgCl$_2$, about 30 mM MgCl$_2$, about 31 mM MgCl$_2$, about 32 mM MgCl$_2$, about 33 mM MgCl$_2$, about 34 mM MgCl$_2$, about 35 mM MgCl$_2$, about 36 mM MgCl$_2$, about 37 mM MgCl$_2$, about 38 mM MgCl$_2$, about 39 mM MgCl$_2$, about 40 mM MgCl$_2$, about 41 mM MgCl$_2$, about 42 mM MgCl$_2$, about 43 mM MgCl$_2$, about 44 mM MgCl$_2$, about 45 mM MgCl$_2$, about 46 mM MgCl$_2$, about 47 mM MgCl$_2$, about 48 mM MgCl$_2$, about 49 mM MgCl$_2$, or about 50 mM MgCl$_2$. It is understood that recitation of the above discrete values includes a range between each recited value.

A modified simulated body fluid can include at least about 0.05 mM MgSO$_4$. For example, a modified simulated body fluid can include at least about 0.05 mM MgSO$_4$; at least about 0.25 mM MgSO$_4$; at least about 0.5 mM MgSO$_4$; at least about 0.75 mM MgSO$_4$; at least about 1 mM MgSO$_4$; at least about 1.25 mM MgSO$_4$; at least about 1.5 mM MgSO$_4$; at least about 1.75 mM MgSO$_4$; at least about 2 mM MgSO$_4$; at least about 2.25 mM MgSO$_4$; at least about 2.5 mM MgSO$_4$; at least about 2.75 mM MgSO$_4$; at least about 3 mM MgSO$_4$; at least about 3.25 mM MgSO$_4$; at least about 3.5 mM MgSO$_4$; at least about 3.75 mM MgSO$_4$; at least about 4 mM MgSO$_4$; at least about 4.25 mM MgSO$_4$; at least about 4.5 mM MgSO$_4$; at least about 4.75 mM MgSO$_4$; at least about 5 mM MgSO$_4$; at least about 6 mM MgSO$_4$; at least about 7 mM MgSO$_4$; at least about 8 mM MgSO$_4$; at least about 9 mM MgSO$_4$; at least about 10 mM MgSO$_4$; at least about 11 mM MgSO$_4$; at least about 12 mM MgSO$_4$; at least about 13 mM MgSO$_4$; at least about 14 mM MgSO$_4$; at least about 15 mM MgSO$_4$; at least about 16 mM MgSO$_4$; at least about 17 mM MgSO$_4$; at least about 18 mM MgSO$_4$; at least about 19 mM MgSO$_4$; at least about 20 mM MgSO$_4$; at least about 21 mM MgSO$_4$; at least about 22 mM MgSO$_4$; at least about 23 mM MgSO$_4$; at least about 24 mM MgSO$_4$; at least about 25 mM MgSO$_4$; at least about 26 mM MgSO$_4$; at least about 27 mM MgSO$_4$; at least about 28 mM MgSO$_4$; at least about 29 mM MgSO$_4$; at least about 30 mM MgSO$_4$; at least about 31 mM MgSO$_4$; at least about 32 mM MgSO$_4$; at least about 33 mM MgSO$_4$; at least about 34 mM MgSO$_4$; at least about 35 mM MgSO$_4$; at least about 36 mM MgSO$_4$; at least about 37 mM MgSO$_4$; at least about 38 mM MgSO$_4$; at least about 39 mM MgSO$_4$; at least about 40 mM MgSO$_4$; at least about 41 mM MgSO$_4$; at least about 42 mM MgSO$_4$; at least about 43 mM MgSO$_4$; at least about 44 mM MgSO$_4$; at least about 45 mM MgSO$_4$; at least about 46 mM MgSO$_4$; at least about 47 mM MgSO$_4$; at least about 48 mM MgSO$_4$; at least about 49 mM MgSO$_4$; or at least about 50 mM MgSO$_4$. It is understood that recitation of the above discrete values includes a range between each recited value.

As another example, a modified simulated body fluid can include about 0.05 mM MgSO$_4$; about 0.25 mM MgSO$_4$; about 0.5 mM MgSO$_4$; about 0.75 mM MgSO$_4$; about 1 mM MgSO$_4$; about 1.25 mM MgSO$_4$; about 1.5 mM MgSO$_4$; about 1.75 mM MgSO$_4$; about 2 mM MgSO$_4$; about 2.25 mM MgSO$_4$; about 2.5 mM MgSO$_4$; about 2.75 mM MgSO$_4$; about 3 mM MgSO$_4$; about 3.25 mM MgSO$_4$; about 3.5 mM MgSO$_4$; about 3.75 mM MgSO$_4$; about 4 mM MgSO$_4$; about 4.25 mM MgSO$_4$; about 4.5 mM MgSO$_4$; about 4.75 mM MgSO$_4$; about 5 mM MgSO$_4$; about 6 mM MgSO$_4$; about 7 mM MgSO$_4$; about 8 mM MgSO$_4$; about 9 mM MgSO$_4$; about 10 mM MgSO$_4$; about 11 mM MgSO$_4$; about 12 mM MgSO$_4$; about 13 mM MgSO$_4$; about 14 mM MgSO$_4$; about 15 mM MgSO$_4$; about 16 mM MgSO$_4$; about 17 mM MgSO$_4$; about 18 mM MgSO$_4$; about 19 mM MgSO$_4$; about 20 mM MgSO$_4$; about 21 mM MgSO$_4$; about 22 mM MgSO$_4$; about 23 mM MgSO$_4$; about 24 mM MgSO$_4$; about 25 mM MgSO$_4$; about 26 mM MgSO$_4$; about 27 mM MgSO$_4$; about 28 mM MgSO$_4$; about 29 mM MgSO$_4$; about 30 mM MgSO$_4$; about 31 mM MgSO$_4$; about 32 mM MgSO$_4$; about 33 mM MgSO$_4$; about 34 mM MgSO$_4$; about 35 mM MgSO$_4$; about 36 mM MgSO$_4$; about 37 mM MgSO$_4$; about 38 mM MgSO$_4$; about 39 mM MgSO$_4$; about 40 mM MgSO$_4$; about 41 mM MgSO$_4$; about 42 mM MgSO$_4$; about 43 mM MgSO$_4$; about 44 mM MgSO$_4$; about 45 mM MgSO$_4$; about 46 mM MgSO$_4$; about 47 mM MgSO$_4$; about 48 mM MgSO$_4$; about 49 mM MgSO$_4$; or about 50 mM MgSO$_4$. It is understood that recitation of the above discrete values includes a range between each recited value.

A modified simulated body fluid can include at least about 0.4 mM NaHCO$_3$. For example, a modified simulated body fluid can include at least about 0.4 mM NaHCO$_3$; at least about 0.6 mM NaHCO$_3$; at least about 0.8 mM NaHCO$_3$; at least about 1.0 mM NaHCO$_3$; at least about 1.2 mM NaHCO$_3$; at least about 1.4 mM NaHCO$_3$; at least about 1.6 mM NaHCO$_3$; at least about 1.8 mM NaHCO$_3$; at least about 2.0 mM NaHCO$_3$; at least about 2.2 mM NaHCO$_3$; at least about 2.4 mM NaHCO$_3$; at least about 2.6 mM NaHCO$_3$; at least about 2.8 mM NaHCO$_3$; at least about 3.0 mM NaHCO$_3$; at least about 3.2 mM NaHCO$_3$; at least about 3.4 mM NaHCO$_3$; at least about 3.6 mM NaHCO$_3$; at least about 3.8 mM NaHCO$_3$; at least about 4.0 mM NaHCO$_3$; at least about 4.2 mM NaHCO$_3$; at least about 4.4 mM NaHCO$_3$; at least about 4.6 mM NaHCO$_3$; at least about 4.8 mM NaHCO$_3$; at least about 5.0 mM NaHCO$_3$; at least about 5.2 mM NaHCO$_3$; at least about 5.4 mM NaHCO$_3$; at least about 5.6 mM NaHCO$_3$; at least about 5.8 mM NaHCO$_3$; at least about 6.0 mM NaHCO$_3$; at least about 6.2 mM NaHCO$_3$; at least about 6.4 mM NaHCO$_3$; at least about 6.6 mM NaHCO$_3$; at least about 6.8 mM NaHCO$_3$; at least about 7.0 mM NaHCO$_3$; at least about 7.2 mM NaHCO$_3$; at least about 7.4 mM NaHCO$_3$; at least about 7.6 mM NaHCO$_3$; at least about 7.8 mM NaHCO$_3$; at least about 8.0 mM NaHCO$_3$; at least about 8.2 mM NaHCO$_3$; at least about 8.4 mM NaHCO$_3$; at least about 8.6 mM NaHCO$_3$; at least about 8.8 mM NaHCO$_3$; at least about 9.0 mM NaHCO$_3$; at least about 10 mM NaHCO$_3$; at least about 20 mM NaHCO$_3$; at least about 30 mM NaHCO$_3$; at least about 40 mM NaHCO$_3$; at least about 50 mM NaHCO$_3$; at least about 60 mM NaHCO$_3$; at least about 70 mM NaHCO$_3$; at least about 80 mM NaHCO$_3$; at least about 90 mM NaHCO$_3$; at least about 100 mM NaHCO$_3$; at least about 200 mM NaHCO$_3$; at least about 300 mM NaHCO$_3$; at least about 400 mM NaHCO$_3$; at least about 500 mM NaHCO$_3$; at least about 600 mM NaHCO$_3$; at least about 700 mM NaHCO$_3$; at least about 800 mM NaHCO$_3$; at least about 900 mM NaHCO$_3$; or at least about 1000 mM NaHCO$_3$. It is understood that recitation of the above discrete values includes a range between each recited value.

As another example, a modified simulated body fluid can include about 0.4 mM NaHCO$_3$; about 0.6 mM NaHCO$_3$; about 0.8 mM NaHCO$_3$; about 1.0 mM NaHCO$_3$; about 1.2 mM NaHCO$_3$; about 1.4 mM NaHCO$_3$; about 1.6 mM NaHCO$_3$; about 1.8 mM NaHCO$_3$; about 2.0 mM NaHCO$_3$; about 2.2 mM NaHCO$_3$; about 2.4 mM NaHCO$_3$; about 2.6 mM NaHCO$_3$; about 2.8 mM NaHCO$_3$; about 3.0 mM NaHCO$_3$; about 3.2 mM NaHCO$_3$; about 3.4 mM NaHCO$_3$; about 3.6 mM NaHCO$_3$; about 3.8 mM NaHCO$_3$; about 4.0 mM NaHCO$_3$; about 4.2 mM NaHCO$_3$; about 4.4 mM NaHCO$_3$; about 4.6 mM NaHCO$_3$; about 4.8 mM NaHCO$_3$; about 5.0 mM NaHCO$_3$; about 5.2 mM NaHCO$_3$; about 5.4 mM NaHCO$_3$; about 5.6 mM NaHCO$_3$; about 5.8 mM NaHCO$_3$; about 6.0 mM NaHCO$_3$; about 6.2 mM NaHCO$_3$; about 6.4 mM NaHCO$_3$; about 6.6 mM NaHCO$_3$; about 6.8 mM NaHCO$_3$; about 7.0 mM NaHCO$_3$; about 7.2 mM NaHCO$_3$; about 7.4 mM NaHCO$_3$; about 7.6 mM NaHCO$_3$; about 7.8 mM NaHCO$_3$; about 8.0 mM NaHCO$_3$; about 8.2 mM NaHCO$_3$; about 8.4 mM NaHCO$_3$; about 8.6 mM NaHCO$_3$; about 8.8 mM NaHCO$_3$; about 9.0 mM NaHCO$_3$; about 10 mM NaHCO$_3$; about 20 mM NaHCO$_3$; about 30 mM NaHCO$_3$; about 40 mM NaHCO$_3$; about 50 mM NaHCO$_3$; about 60 mM NaHCO$_3$; about 70 mM NaHCO$_3$; about 80 mM NaHCO$_3$; about 90 mM NaHCO$_3$; about 100 mM NaHCO$_3$; about 200 mM NaHCO$_3$; about 300 mM NaHCO$_3$; about 400 mM NaHCO$_3$; about 500 mM NaHCO$_3$; about 600 mM NaHCO$_3$; about 700 mM NaHCO$_3$; about 800 mM NaHCO$_3$; about 900 mM NaHCO$_3$; or about 1000 mM NaHCO$_3$. It is understood that recitation of the above discrete values includes a range between each recited value.

A modified simulated body fluid can include at least about 0.5 mM CaCl$_2$). For example, a modified simulated body fluid can include at least about 0.5 mM CaCl2, at least about 1.0 mM CaCl$_2$), at least about 1.5 mM CaCl$_2$), at least about 2.0 mM CaCl$_2$), at least about 2.5 mM CaCl$_2$), at least about 3.0 mM CaCl$_2$), at least about 3.5 mM CaCl$_2$), at least about 4.0 mM CaCl$_2$), at least about 4.5 mM CaCl$_2$), at least about 5.0 mM CaCl$_2$), at least about 5.5 mM CaCl$_2$), at least about 6.0 mM CaCl$_2$), at least about 6.5 mM CaCl$_2$), at least about 7.0 mM CaCl$_2$), at least about 7.5 mM CaCl$_2$), at least about 8.0 mM CaCl$_2$), at least about 8.5 mM CaCl$_2$), at least about 9.0 mM CaCl$_2$), at least about 9.5 mM CaCl$_2$), at least about 10.0 mM CaCl$_2$), at least about 10.5 mM CaCl$_2$), at least about 11.0 mM CaCl$_2$), at least about 11.5 mM CaCl$_2$), at least about 12.0 mM CaCl$_2$), at least about 12.5 mM CaCl$_2$), at least about 13.0 mM CaCl$_2$), at least about 13.5 mM CaCl$_2$), at least about 14.0 mM CaCl$_2$), at least about 14.5 mM CaCl$_2$), at least about 15.0 mM CaCl$_2$), at least about 15.5 mM CaCl$_2$), at least about 16.0 mM CaCl$_2$), at least about 16.5 mM CaCl$_2$), at least about 17.0 mM CaCl$_2$), at least about 17.5 mM CaCl$_2$), at least about 18.0 mM CaCl$_2$), at least about 18.5 mM CaCl$_2$), at least about 19.0 mM CaCl$_2$), at least about 19.5 mM CaCl$_2$), at least about 20.0 mM CaCl$_2$), at least about 25 mM CaCl$_2$), at least about 30 mM CaCl$_2$), at least about 35 mM CaCl$_2$), at least about 40 mM CaCl$_2$), at least about 45 mM CaCl$_2$), or at least about 50 mM CaCl$_2$). It is understood that recitation of the above discrete values includes a range between each recited value.

As another example, a modified simulated body fluid can include about 0.5 mM CaCl$_2$), about 1.0 mM CaCl$_2$), about 1.5 mM CaCl$_2$), about 2.0 mM CaCl$_2$); about 2.5 mM CaCl$_2$), about 3.0 mM CaCl$_2$), about 3.5 mM CaCl$_2$), about 4.0 mM CaCl$_2$), about 4.5 mM CaCl$_2$), about 5.0 mM CaCl$_2$), about 5.5 mM CaCl$_2$), about 6.0 mM CaCl$_2$), about 6.5 mM CaCl$_2$), about 7.0 mM CaCl$_2$), about 7.5 mM CaCl$_2$); about 8.0 mM CaCl$_2$), about 8.5 mM CaCl$_2$), about 9.0 mM CaCl$_2$), about 9.5 mM CaCl$_2$), about 10.0 mM CaCl$_2$), about 10.5 mM CaCl$_2$), about 11.0 mM CaCl$_2$); about 11.5 mM CaCl$_2$), about 12.0 mM CaCl$_2$), about 12.5 mM CaCl$_2$), about 13.0 mM CaCl$_2$), about 13.5 mM CaCl$_2$), about 14.0 mM CaCl$_2$), about 14.5 mM CaCl$_2$); about 15.0 mM CaCl$_2$), about 15.5 mM CaCl$_2$), about 16.0 mM CaCl$_2$), about 16.5 mM CaCl$_2$), about 17.0 mM CaCl$_2$), about 17.5 mM CaCl$_2$), about 18.0 mM CaCl$_2$); about 18.5 mM CaCl$_2$), about 19.0 mM CaCl$_2$), about 19.5 mM CaCl$_2$), about 20.0 mM CaCl$_2$), about 25 mM CaCl$_2$), about 30 mM CaCl$_2$), about 35 mM CaCl$_2$), about 40 mM CaCl$_2$), about 45 mM CaCl$_2$), or about 50 mM CaCl$_2$). It is understood that recitation of the above discrete values includes a range between each recited value.

A modified simulated body fluid can include at least about 0.2 mM KH$_2$PO$_4$. For example, a modified simulated body fluid can include at least about 0.2 mM KH$_2$PO$_4$; at least about 0.4 mM KH$_2$PO$_4$; at least about 0.6 mM KH$_2$PO$_4$; at least about 0.8 mM KH$_2$PO$_4$; at least about 1.0 mM KH$_2$PO$_4$; at least about 1.2 mM KH$_2$PO$_4$; at least about 1.4 mM KH$_2$PO$_4$; at least about 1.6 mM KH$_2$PO$_4$; at least about 1.8 mM KH$_2$PO$_4$; at least about 2.0 mM KH$_2$PO$_4$; at least about 2.2 mM KH$_2$PO$_4$; at least about 2.4 mM KH$_2$PO$_4$; at least about 2.6 mM KH$_2$PO$_4$; at least about 2.8 mM KH$_2$PO$_4$; at least about 3.0 mM KH$_2$PO$_4$; at least about 3.2 mM KH$_2$PO$_4$; at least about 3.4 mM KH$_2$PO$_4$; at least about 3.6 mM KH$_2$PO$_4$; at least about 3.8 mM KH$_2$PO$_4$; at least about 4.0 mM KH$_2$PO$_4$; at least about 4.2 mM KH$_2$PO$_4$; at least about 4.4 mM KH$_2$PO$_4$; at least about 4.6 mM KH$_2$PO$_4$; at least about 4.8 mM KH$_2$PO$_4$; at least about 5.0 mM KH$_2$PO$_4$; at least about 5.2 mM KH$_2$PO$_4$; at least about 5.4 mM KH$_2$PO$_4$; at least about 5.6 mM KH$_2$PO$_4$; at least about 5.8 mM KH$_2$PO$_4$; at least about 6.0 mM KH$_2$PO$_4$; at least about 6.2 mM KH$_2$PO$_4$; at least about 6.4 mM KH$_2$PO$_4$; at least about 6.6 mM KH$_2$PO$_4$; at least about 6.8 mM KH$_2$PO$_4$; at least about 7.0 mM KH$_2$PO$_4$; at least about 7.2 mM KH$_2$PO$_4$; at least about 7.4 mM KH$_2$PO$_4$; at least about 7.6 mM KH$_2$PO$_4$; at least about 7.8 mM KH$_2$PO$_4$; at least about 8.0 mM KH$_2$PO$_4$; at least about 8.2 mM KH$_2$PO$_4$; at least about 8.4 mM KH$_2$PO$_4$; at least about 8.6 mM KH$_2$PO$_4$; at least about 8.8 mM KH$_2$PO$_4$; at least about 9.0 mM KH$_2$PO$_4$; at least about 9.2 mM KH$_2$PO$_4$; at least about 9.4 mM KH$_2$PO$_4$; at least about 9.6 mM KH$_2$PO$_4$; at least about 9.8 mM KH$_2$PO$_4$; at least about 10.0 mM KH$_2$PO$_4$; at least about 20 mM KH$_2$PO$_4$; at least about 30 mM KH$_2$PO$_4$; at least about 40 mM KH$_2$PO$_4$; at least about 50 mM KH$_2$PO$_4$; at least about 60 mM KH$_2$PO$_4$; at least about 70 mM KH$_2$PO$_4$; at least about 80 mM KH$_2$PO$_4$; at least about 90 mM KH$_2$PO$_4$; at least about 100 mM KH$_2$PO$_4$; at least about 110 mM KH$_2$PO$_4$; at least about 120 mM KH$_2$PO$_4$; at least about 130 mM KH$_2$PO$_4$; at least about 140 mM KH$_2$PO$_4$; at least about 150 mM KH$_2$PO$_4$; at least about 160 mM KH$_2$PO$_4$; at least about 170 mM KH$_2$PO$_4$; at least about 180 mM KH$_2$PO$_4$; at least about 190 mM KH$_2$PO$_4$; or at least about 200 mM KH$_2$PO$_4$. It is understood that recitation of the above discrete values includes a range between each recited value.

As another example, a modified simulated body fluid can include about 0.2 mM KH$_2$PO$_4$; about 0.4 mM KH$_2$PO$_4$; about 0.6 mM KH$_2$PO$_4$; about 0.8 mM KH$_2$PO$_4$; about 1.0 mM KH$_2$PO$_4$; about 1.2 mM KH$_2$PO$_4$; about 1.4 mM KH$_2$PO$_4$; about 1.6 mM KH$_2$PO$_4$; about 1.8 mM KH$_2$PO$_4$; about 2.0 mM KH$_2$PO$_4$; about 2.2 mM KH$_2$PO$_4$; about 2.4 mM KH$_2$PO$_4$; about 2.6 mM KH$_2$PO$_4$; about 2.8 mM KH$_2$PO$_4$; about 3.0 mM KH$_2$PO$_4$; about 3.2 mM KH$_2$PO$_4$; about 3.4 mM KH$_2$PO$_4$; about 3.6 mM KH$_2$PO$_4$; about 3.8 mM KH$_2$PO$_4$; about 4.0 mM KH$_2$PO$_4$; about 4.2 mM KH$_2$PO$_4$; about 4.4 mM KH$_2$PO$_4$; about 4.6 mM KH$_2$PO$_4$; about 4.8 mM KH$_2$PO$_4$; about 5.0 mM KH$_2$PO$_4$; about 5.2 mM KH$_2$PO$_4$; about 5.4 mM KH$_2$PO$_4$; about 5.6 mM KH$_2$PO$_4$; about 5.8 mM KH$_2$PO$_4$; about 6.0 mM KH$_2$PO$_4$; about 6.2 mM KH$_2$PO$_4$; about 6.4 mM KH$_2$PO$_4$; about 6.8 mM KH$_2$PO$_4$; about 7.0 mM KH$_2$PO$_4$; about 7.2 mM KH$_2$PO$_4$; about 7.4 mM KH$_2$PO$_4$; about 7.6 mM KH$_2$PO$_4$; about 7.8 mM KH$_2$PO$_4$; about 8.0 mM KH$_2$PO$_4$; about 8.2 mM KH$_2$PO$_4$; about 8.4 mM KH$_2$PO$_4$; about 8.6 mM KH$_2$PO$_4$; about 8.8 mM KH$_2$PO$_4$; about 9.0 mM KH$_2$PO$_4$; about 9.2 mM KH$_2$PO$_4$; about 9.4 mM KH$_2$PO$_4$; about 9.6 mM KH$_2$PO$_4$; about 9.8 mM KH$_2$PO$_4$; about 10.0 mM KH$_2$PO$_4$; about 20 mM KH$_2$PO$_4$; about 30 mM KH$_2$PO$_4$; about 40 mM KH$_2$PO$_4$; about 50 mM KH$_2$PO$_4$; about 60 mM KH$_2$PO$_4$; about 70 mM KH$_2$PO$_4$; about 80 mM KH$_2$PO$_4$; about 90 mM KH$_2$PO$_4$; about 100 mM KH$_2$PO$_4$; about 110 mM KH$_2$PO$_4$; about 120 mM KH$_2$PO$_4$; about 130 mM KH$_2$PO$_4$; about 140 mM KH$_2$PO$_4$; about 150 mM KH$_2$PO$_4$; about 160 mM KH$_2$PO$_4$; about 170 mM KH$_2$PO$_4$; about 180 mM KH$_2$PO$_4$; about 190 mM KH$_2$PO$_4$; or about 200 mM KH$_2$PO$_4$. It is understood that recitation of the above discrete values includes a range between each recited value.

In some embodiments, the solution can comprise a surfactant, which can change the morphology of the calcium-containing mineral layer. Any surfactant now known or later discovered may be used here. In some embodiments, the surfactant can be Tween 20™.

Lyophilized Porous Macroparticles

The plurality of lyophilized porous macroparticles can comprise a ceramic material in an amount from about 50 to about 98 wt. % and a polymer in an amount from about 2 to about 50 wt. % based on a total weight of each of the lyophilized porous macroparticles as more particularly described in International Application No. PCT/2020/050482 filed on Sep. 11, 2020, incorporated herein by reference in its entirety. The plurality of lyophilized porous macroparticles can each include from about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 to about 98 wt. % ceramic material and from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 wt. % polymer based on the total weight of each of the lyophilized porous macroparticles. The ceramic material can comprise synthetic ceramic or ceramics including hydroxyapatite and beta-tricalcium phosphate. The ceramic material can be in a powder form. The ceramic material comprises a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

The ceramic material of the lyophilized porous macroparticles is a biphasic calcium phosphate comprising hydroxyapatite in an amount of about 8 to about 22 wt. % and beta-tricalcium phosphate in an amount of about 78 to about 92 wt. %. In some embodiments, the hydroxyapatite is in an amount of about 8, 9, 10, 11, 12, 13, 14, 15, 16, 17, 18, 19, 20, 21 to about 22 wt. % and the beta-tricalcium phosphate in an amount of about 78, 79, 80, 81, 82, 83, 84, 85, 86, 87, 88, 89, 90, 91 to about 92 wt. %.

The porous ceramic particles comprise hydroxyapatite and beta-tricalcium phosphate. The hydroxyapatite is in an amount of about 8 to about 22 wt. % based on a total weight of a ceramic granule. The hydroxyapatite can be in a range from about 8, 9, 10, 11, 12, 13, 14, 15, 16, 17, 18, 19, 20, 21 to about 22 wt. %. In some embodiments, the hydroxyapatite can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

The beta-tricalcium phosphate is in an amount of about 78 to about 92 wt. % based on a total weight of a ceramic granule. The beta-tricalcium phosphate can be in an amount from about 78, 79, 80, 81, 82, 83, 84, 85, 86, 87, 88, 89, 90, 91 to about 92 wt. %. In some embodiments, the beta-tricalcium phosphate can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

The porous ceramic particles can have a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

In some embodiments, the lyophilized porous macroparticles comprise collagen-containing biomaterials from the implant market which, when placed in a bone defect, provide scaffolding around which the patient's new bone and/or cartilage will grow, gradually replacing the carrier matrix as the target site heals. In other embodiments, ceramic particles coated with mineral coatings can be embedded in a porous carrier matrix such as cross-linked or noncross-linked collagen, carboxymethyl cellulose or alginate that can also include identification or surface markers that distinguish them from uncoated ceramic particles. Examples of suitable lyophilized porous macroparticles may include, but are not limited to, the MasterGraft® Matrix produced by Medtronic Sofamor Danck, Inc., Memphis, Tenn.; MasterGraft® Putty produced by Medtronic Sofamor Danek, Inc., Memphis, Tenn. The MasterGraft® Matrix or the MasterGraft® Putty are synthetic bone grafts containing biphasic calcium phosphate (85% beta-tricalcium phosphate (β-TCP) and 15% hydroxyapatite (HA) in porous granules alone or in combination with bovine type I collagen. In some embodiments, each macroparticle contains 15% hydroxyapatite and 85% beta-tricalcium phosphate (β-TCP). This ratio provides long term stability and a good resorption rate. In other embodiments, each macroparticle can contain 2.5%+/−0.25% collagen and 97.5%+/−0.25% β-TCP.

The polymer component of each of the plurality of lyophilized porous macroparticles can be porcine or bovine collagen, bovine type I collagen, tendon or dermis derived collagen, or a combination thereof.

Each of the plurality of lyophilized porous macroparticles have an average diameter from about 0.1 mm to about 10 mm. For example, each of the lyophilized porous macroparticles can have an average diameter from about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 to about 10 mm. In some embodiments, the lyophilized porous macroparticle can have a granule size from about 0.09 mm to about 0.6 mm.

Each of the lyophilized porous macroparticles can have an average height and/or length from about 0.05, 0.01 mm to about 10 mm or from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 mm.

The ceramic material provided in each of the lyophilized porous macroparticles can be in the form of porous ceramic granules. The porous ceramic granules are like the granules found and described in U.S. application Ser. No. 16/523,259, filed on Jul. 26, 2019, assigned to Warsaw Orthopedic, Inc., which is incorporated herein by reference in its entirety. The porous ceramic granules have an average diameter from about 50 μm to 1.6 mm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 850, 900, 950, 1000, 1100, 1150, 1200, 1250, 1300, 1350, 1400, 1450, 1500, 1550 to about 1600 μm. It is to be understood that the ceramic material is smaller in size than the macroparticles.

When the porous ceramic granules are used in the composition, the granules are in an amount from about 50 to about 98 wt. % and the collagen is in an amount from about 2 to about 50 wt. % based on a total weight of each of the lyophilized porous macroparticles. Each of the porous ceramic granules comprise hydroxyapatite and beta-tricalcium phosphate having a calcium to phosphate ratio of between 1.0 to about 2.0, as described above regarding the ceramic material.

Each of the porous ceramic granules have a Brunauer-Emmett-Teller (BET) surface area from about 0.2 to about 10 $m^2/g$. The BET surface area can be from about 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 $m^2/g$. The increase in surface area further facilitates new bone growth by allowing the granules to dissolve and release calcium faster than a granule would.

Each of the porous ceramic granules can have a microporosity, and the diameter of the micropores is from about 0.01 to about 10 microns. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 microns. In some embodiments, the median pore diameter can be about 125 μm and the average pore diameter can be 78 μm.

The plurality of lyophilized porous macroparticles can be made into a variety of shapes after lyophilization or using cryogel applications. The shapes can be cut from a textured or flat shaped sheet of bone material comprising the ceramic material and polymer or can be prepared as individual macroparticles created in molds. The macroparticles are porous, but in some embodiments, the macroparticles are highly porous. For example, porous macroparticles can include that the macroparticles have a porosity from about 10 to about 80% or from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 to about 80%. Highly porous macroparticles can include that the macroparticles have a porosity from about 81 to about 99% or from about 81, 82, 83, 84, 85, 86, 87, 88, 89, 90, 91, 92, 93, 94, 95, 96, 97, 98 to about 99%.

The macroparticle shapes and size create a high level of surface area which increases uniform hydration when fluid is administered to the macroparticles. For example, due to the high level of surface area, fluid will rapidly move into the macroparticles through wicking. The macroparticle shapes can include cylinders; cubes; rods or tubes; a hollow tube or tubes; a half hemispherical hollow tube or tubes; a rectangle or rectangles; a disc or discs; electro-spun fibers or a combination thereof.

The plurality of lyophilized porous macroparticles in the chamber can have a packing density to maximize hydration of the plurality of lyophilized porous macroparticles when fluid is introduced. In some embodiments, the packing density can be high. The packing density of a MasterGraft® product can be from about 1 to about 5 g/cm$^3$, from about 1 to about 4 g/cm$^3$, from about 1 to about 3 g/cm$^3$, or from about 1 to about 2 g/cm$^3$. The packing density can be from about 1, 2, 3, 4 to about 5 g/cm$^3$. In some embodiments, the packing density of the macroparticles combined with the high surface area of the macroparticles, creates a uniformly hydrated composition that does not agglomerate and is flowable.

The fluid used to hydrate the macroparticles can include bone marrow aspirate, saline, sterile water, blood for injection, phosphate buffered saline, dextrose, Ringer's lactated solution, or a combination thereof. The ratio of fluid to the plurality of lyophilized porous macroparticles can be from about 0.5:1 to about 3:1. In some embodiments, the ratio of fluid to the plurality of lyophilized porous macroparticles can be from about 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1 to about 3:1.

Autograft bone can be added to the hydratable composition before or after hydration. The autograft bone can be cut into various shapes, including fibers, chips, granules, powder, shards, shavings, or a combination thereof. The autograft bone can be cut into specific sizes. For example, the autograft bone can be from about 1 to about 10 mm. In some embodiments, the size of the autograft bone added to the composition can be from about 1, 2, 3, 4, 5, 6, 7, 8, 9 to about 10 mm. In some embodiments, the autograft bone is cut into bone chips having a size from about 1 to about 4 mm and is added to the hydratable composition after hydration.

A certain amount of autograft bone can be added to the hydratable composition, such as from about 0 to about 50 vol. % or from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 vol. % based on the total weight of the hydratable composition. In some embodiments, the composition can contain greater than 50 vol. % of autograft bone without the composition losing its cohesive properties.

In some embodiments, the hydratable composition has a flowable viscosity starting from about 50 Pascal-second (Pa-s), 100 Pa-s, 150 Pa-s, 200 Pa-s, 250 Pa-s, to about 300 Pa-s and reaches a higher viscosity from about 500 Pa-s, 750 Pa-s, 1000 Pa-s, 1,500 Pa-s, 2,000 Pa-s, 2,500 Pa-s to about 3,000 Pa-s. In some embodiments, the hydratable composition has a flowable viscosity starting from about 50 Pa-s to about 3,000 Pa-s and reaches a higher viscosity from about 3,000 Pa-s to about 300,000 Pa-s.

The hydratable composition can have a certain density when hydrated. For example, when the composition is hydrated, the density can be from about 1.2 to about 2.0 g/cc or from about 1.4 to about 1.6 g/cc. In some embodiments, the hydrated composition can have a density from about 1.2, 1.3, 1.4, 1.5, 1.6, 1.7, 1.8, 1.9 to about 2.0 g/cc.

The hydratable composition can have a modulus of elasticity from about 2 MPa to about 12 MPa, such as from about 2, 3, 4, 5, 6, 7, 8, 9, 10, 11 to about 12 MPa.

In some embodiments, if autograft bone is added to the composition after hydration, the modulus of elasticity can be increased with the addition of the autograft bone.

In some embodiments, the fluid used to hydrate the composition can include sterile water, saline, phosphate buffered saline (PBS), hyaluronic acid, cellulose ethers (such as carboxymethyl cellulose), water, collagen, gelatin, autoclaved bone powder, osteoconductive carriers, whole blood, blood fractions, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma.

In some embodiments, additional or alternative materials may be added to the composition such as one or more of poly (alpha-hydroxy acids), polyglycolide (PG), polyethylene glycol (PEG) conjugates of poly (alpha-hydroxy acids), polyorthoesters (POE), polyaspirins, polyphosphagenes, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrrolidone, polyamide, oxycellulose, copolymer of glycolic acid and trimethylene carbonate, polyesteramides, polyether ether ketone, polymethylmethacrylate, silicone, hyaluronic acid, or combinations thereof.

In some embodiments, the macroparticles can alternatively or in addition to comprise at least one biodegradable polymer comprising one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly (L-lactide-co-caprolactone), poly(D-lactide-co-caprolactone), poly(D,L-lactide), poly(D-lactide), poly(L-lactide), poly(esteramide), carboxymethylcellulose (CMC), alkylene oxide copolymer (AOC) or a combination thereof.

In some embodiments, the macroparticles can alternatively, or in addition to, comprise at least one ceramic material, including, but not limited to synthetic ceramics selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may be used. In some embodiments, the ceramic material is tri-calcium phosphate or biphasic calcium phosphate and silicon ceramics. In some embodiments, the ceramic material is tricalcium phosphate. In other embodiments, the macroparticles can include materials such as demineralized bone matrices (DBMs), stem cells, growth factors or combinations thereof.

In some embodiments, the ceramic material is a combination of a calcium phosphate ceramic and a silicon ceramic. In some embodiments, the calcium phosphate ceramic is resorbable biphasic calcium phosphate (BCP) or resorbable tri-calcium phosphate (TCP).

The ceramic material of the disclosure may also be oxide ceramics such as alumina ($Al_2O_3$) or zirconia ($ZrO_2$) or composite combinations of oxides and non-oxides such as silicon nitride.

In various embodiments, the plurality of lyophilized porous macroparticles comprise ceramic material in an amount from about 50 to about 98 wt. % and collagen in an amount from about 2 to about 50 wt. % based on a total weight of each of the lyophilized porous macroparticles, each of the lyophilized porous macroparticles having an average diameter from about 0.1 mm to about 10 mm. In other embodiments, the bone implant described in this application is rollable and has a thickness of from about 1 mm to about 4 mm and comprises up to 83% ceramic material. In some embodiments, the bone implant has a surface area of at least about 5 m$^2$/g. 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 m$^2$/g.

Coatings

Coating materials comprise various materials designed to be deposited on the surface of the bone materials. Exemplary methods for producing a primer coated scaffold (e.g., bone material) using a primer coating composition comprising a polymer are described herein. For example, the primer coating composition can be a solution comprising a polymer and a solvent. As another example, the primer coating composition can be any composition comprising a polymer. The primer coating composition can be in solution state, solid state, liquid state, gas state, plasma state, or vapor phase. As another example, the primer coating composition can be a powder.

As described herein, the composition of a polymer layer on a scaffold can be manipulated by adjusting the primer coating composition, such as the polymer composition (e.g., type, concentration), additives, or solvent composition (e.g., type, concentration) in the primer coating composition.

Polymers

Embodiments include exemplary methods for producing a primer coated scaffold using a polymer containing coating composition in solution. For example, a polymer containing primer coating composition can include any conventional polymer (see e.g., Nair et al. Prog. Poly. Sci 2007 32(8-9) 762-798; Miller Chou et al. Prog. Poly. Sci 2003 28 1223-1270). As another example, a polymer in a polymer containing primer coating composition can include one or more of acrylic resin, alginate, caprolactone, collagen, chitosan, hyaluronic acid, hydrogel, hydroxybutyric acid, polyanhydride, polycaprolactone (PCL), poly(dimethylglycolic acid), polydioxanone (PDO), polyester, polyethylene, poly(ethylene glycol), poly(glycolide) (PGA), poly(glycolic acid), polyhydroxobutyrate, poly(2-hydroxyethyl-methacrylate), poly-lactide-co-glycolide (PLCG), poly(D,L-lactide-co-glycolide) (PLG), poly(lactide-co-glycolic acid) (PLGA), polylactide (PLA), polylactic acid (PLLA), poly-lactide-co-glycolide (PLCG), poly(methylethylglycolic acid), polymethylmethacrylate, polyphosphazenes, polyphosphoesters, polypropylene, poly(propylene fumarate), polyurethane (PU), silicone rubber, or combinations or copolymers thereof.

As another example, a polymer in a polymer containing primer coating can include one or more of a bioresorbable polyester or its copolymers. The biodegradable polyester or its copolymer can be, for example, one or more of the following: polycaprolactone (PCL), poly(D,L-lactide-co-glycolide) (PLG), polylactide (PLA), polylactic acid (PLLA), or poly-lactide-co-glycolide (FLCG).

The primer coating composition, as described herein, can include two polymers. For example, the polymer containing primer coating composition, as described herein, can comprise a ratio of two polymers of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, or about 1:40. It is understood that recitation of the above discrete values includes a range between each recited value.

The primer coating composition can include a powder comprising one or more polymers as described herein. The powder can comprise a range of particle grain sizes. The powder can comprise an average grain size. For example, the powder can include a grain size or an average grain size of about 1 µm to about 5,000 µm. As another example, the powder can include a grain size or an average grain size of about 10 µm to about 500 µm. As another example, the powder can include a grain size or an average grain size of about 1 µm; about 2 µm; about 3 µm; about 4 µm; about 5 µm; about 6 µm; about 7 µm; about 8 µm; about 9 µm; about 10 µm; about 11 µm; about 12 µm; about 13 µm; about 14 µm; about 15 µm; about 16 µm; about 17 µm; about 18 µm; about 19 µm; about 20 µm; about 21 µm; about 22 µm; about 23 µm; about 24 µm; about 25 µm; about 26 µm; about 27 µm; about 28 µm; about 29 µm; about 30 µm; about 31 µm; about 32 µm; about 33 µm; about 34 µm; about 35 µm; about 36 µm; about 37 µm; about 38 µm; about 39 µm; about 40 µm; about 41 µm; about 42 µm; about 43 µm; about 44 µm; about 45 µm; about 46 µm; about 47 µm; about 48 µm; about 49 µm; about 50 µm; about 60 µm; about 70 µm; about 80 µm; about 90 µm; about 100 µm; about 110 µm; about 120 µm; about 130 µm; about 140 µm; about 150 µm; about 160 µm; about 170 µm; about 180 µm; about 190 µm; about 200 µm; about 210 µm; about 220 µm; about 230 µm; about 240 µm; about 250 µm; about 260 µm; about 270 µm; about 280 µm; about 290 µm; about 300 µm; about 310 µm; about 320 µm; about 330 µm; about 340 µm; about 350 µm; about 360 µm; about 370 µm; about 380 µm; about 390 µm; about 400 µm; about 410 µm; about 420 µm; about 430 µm; about 440 µm; about 450 µm; about 460 µm; about 470 µm; about 480 µm; about 490 µm; or about 500 µm. It is understood that recitation of the above discrete values includes a range between each recited value.

Solvents

In some embodiments, there are exemplary methods for producing a primer coated scaffold (bone material) using a polymer containing coating composition in solution (e.g., primer coating solution). For example, the polymer containing primer coating solution can include any conventional solvent (see e.g., Nair et al. Prog. Poly. Sci 2007 32(8-9) 762-798; Miller Chou et al. Prog. Poly. Sci 2003 28 1223-1270). As another example, the solvent can be sufficient for polymer dissolution (see e.g., Miller-Chou et al. 2003 Prog. Polym. Sci. (28) 1223-1270). As another example, the solvent in the polymer containing primer coating solution can include one or more of acetic acid, alcohols, aliphatic ethers, aniline, aromatic hydrocarbons, chlorinated hydrocarbons, aromatic hydrocarbons, aqueous alkali, aqueous solutions of cupriethylenediamine, benzene, biphenyl, chlorinated aliphatic hydrocarbons, chlorinated hydrocarbons, chloroform, chlorophenol, chlorobenzene, cyclohexanone, chlorinated hydrocarbons, chloroauric acid, DCM, dimethylformamide (DMF), DMSO, dichlorobiphenyl, dioxane, dilute aqueous sodium hydroxide, 1,2-dichlorobenzene, dichloromethane, DCM, ethanol, ethyl acetate, ethylene carbonate, esters, formic acid, glycols, halogenated hydrocarbons, HFIP, higher aliphatic esters or ketones, halogenated hydrocarbons, higher aliphatic esters, higher aliphatic ketones, ketones, higher ketones, hydrocarbons, isopropylamine, methyl ethyl ketone, morpholine, methylene chloride, methanol, methyl ethyl ketone, m-Cresol, NMP, phenol, phenylenediamines, sulfuric acid, tetramethylurea, toluene, trifluoroacetic acid, THD, tetramethylurca,tetrahydrofuran (THF), trifluoroacetic acid, trichloroethanol, Toluene, trichloroethane, trichloroacetaldehyde hydrate, perfluorokerosene, pyridine, phenyl ether, piperazine, pyridine, water, or xylene, or combinations thereof.

The polymer containing primer coating solution, as described herein, can include two solvents. For example, the polymer containing primer coating solution, as described herein, can include a ratio of two solvents of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, or about 1:40. It is understood that recitation of the above discrete values includes a range between each recited value.

The polymer containing primer coating solution, as described herein, can have a weight % of polymer/volume of solvent (% w/v). For example, the polymer containing primer coating solution, as described herein, can have about 0.1% weight polymer/volume of solvent; about 0.2,% weight polymer/volume of solvent; about 0.3% weight polymer/volume of solvent; about 0.4% weight polymer/volume of solvent; about 0.5% weight polymer/volume of solvent; about 0.6% weight polymer/volume of solvent; about 0.7% weight polymer/volume of solvent; about 0.8% weight polymer/volume of solvent; about 0.9% weight polymer/volume of solvent; about 1% weight polymer/volume of solvent; about 2% weight polymer/volume of solvent; about 3% weight polymer/volume of solvent; about 4% weight polymer/volume of solvent; about 5% weight polymer/volume of solvent; about 6% weight polymer/volume of solvent; about 7% weight polymer/volume of solvent; about 8% weight polymer/volume of solvent; about 9% weight polymer/volume of solvent; about 10% weight polymer/volume of solvent; 11% weight polymer/volume of solvent; about 12% weight polymer/volume of solvent; about 13% weight polymer/volume of solvent; about 14% weight polymer/volume of solvent; about 15% weight polymer/volume of solvent; about 16% weight polymer/volume of solvent; about 17% weight polymer/volume of solvent; about 18% weight polymer/volume of solvent; about 19% weight polymer/volume of solvent; about 20% weight polymer/volume of solvent; 21% weight polymer/volume of solvent; about 22% weight polymer/volume of solvent; about 23% weight polymer/volume of solvent; about 24% weight polymer/volume of solvent; about 25% weight polymer/volume of solvent; about 26% weight polymer/volume of solvent; about 27% weight polymer/volume of solvent; about 28% weight polymer/volume of solvent; about 29% weight polymer/volume of solvent; about 30% weight polymer/volume of solvent; 31% weight polymer/volume of solvent; about 32% weight polymer/volume of solvent; about 33% weight polymer/volume of solvent; about 34% weight polymer/volume of solvent; about 35% weight polymer/volume of solvent; about 36% weight polymer/volume of solvent; about 37% weight polymer/volume of solvent; about 38% weight polymer/volume of solvent; about 39% weight polymer/volume of solvent; about 40% weight polymer/volume of solvent; 41% weight polymer/volume of solvent; about 42% weight polymer/volume of solvent; about 43% weight polymer/volume of solvent; about 44% weight polymer/volume of solvent; about 45% weight polymer/volume of solvent; about 46% weight polymer/volume of solvent; about 47% weight polymer/volume of solvent; about 48% weight polymer/volume of solvent; about 49% weight polymer/volume of solvent; about 50% weight polymer/volume of solvent; about 60% weight polymer/volume of solvent; about 70% weight polymer/volume of solvent; about 80% weight polymer/volume of solvent; about 90% weight polymer/volume of solvent; or about 100% weight polymer/volume of solvent. It is understood that recitation of the above discrete values includes a range between each recited value.

A useful mineral coating can be prepared as described in U.S. application Ser. No. 15/060,547 filed Mar. 3, 2016 and published as US 20160271296 A1 and U.S. application Ser. No. 13/879,178 filed Sep. 25, 2009 and published as US 20140161886 A1. These entire disclosures are incorporated herein by reference in their entireties and provide mineral coatings having a plate-like nanostructure to an implant having macro surface markers (e.g., recesses and/or projections). In some embodiments, the plate-like nanostructure comprises nanoparticles having a size range from about 100 to about 200 nanometers.

As described in these patent applications, the mineral coating can be calcium-containing. For example, the calcium-containing mineral coating can include hydroxyapatite (HAP), α-tricalcium phosphate (α-TCP), β-tricalcium phosphate (β-TCP), amorphous calcium phosphate, dicalcium phosphate, octacalcium phosphate, calcium phosphate (CaP), or calcium carbonate. The calcium-containing mineral coating can comprise a plurality of layers, e.g., separate layers having distinct dissolution profiles. Under physiological conditions, solubility of calcium phosphate species can adhere to the following trend: amorphous calcium phosphate >dicalcium phosphate >octacalcium phosphate >β-TCP >HAP. A dicalcium phosphate mineral can have a dissolution rate that is more than fifty times higher than that of HAP. Therefore, creation of a matrix with distinct calcium phosphate layers allows for a broad range of dissolution patterns.

The mineral coating of the lyophilized porous macroparticles, can be provided by incubating the macroparticles. For example, in some embodiments, the mineral coating described herein can be developed by incubating the constituents in modified simulated body fluid (mSBF) for four days or more at a pH of about 6.8 to about 7.4 and at a temperature of about 37° C. The SBF or mSBF can be refreshed daily. This procedure produces a calcium-deficient, carbonate-containing apatite material on alginate and on poly-(α-hydroxy esters) as described in U.S. Pat. No. 6,767,928, incorporated herein by reference. mSBF can include elevated calcium and phosphate. In general, an increase in pH can favor hydroxyapatite growth, while a decrease in pH can favor octacalcium phosphate mineral growth.

In other embodiments, conditions favorable for hydroxyapatite formation can include a pH between about 5.0 and about 8.0 and a calcium concentration multiplied by a phosphate concentration between about $10^{-5}$ and about $10^{-8}$ M. Conditions favorable for octacalcium phosphate formation include a pH between about 6.0 and about 8.0 and a calcium concentration multiplied by a phosphate concentration between about $10^{-5}$ and about $10^{-7.5}$ M. Furthermore, conditions favorable for dicalcium phosphate dehydrate formation can include a pH between about 6.0 and about 8.0 and a calcium concentration multiplied by a phosphate concentration between about $10^{-4}$ and about $10^{-6}$ M.

In yet other embodiments, the pH of mSBF can be varied between about 5.0 and about 6.0 to promote hydroxyapatite formation. Similarly, the pH of mSBF can be varied between about 6.0 and about 6.5 to promote octacalcium phosphate and hydroxyapatite formation. Likewise, the pH of mSBF can be varied between about 6.5 and about 8.0 to promote dicalcium phosphate, octacalcium phosphate, and hydroxyapatite formation.

The mineral coating useful for the lyophilized porous macroparticles of the bone implant described in this application can be similar in structure and composition to human bone mineral. For example, the mineral coating can include spherical clusters with a plate-like structure or a plate-like structure and a carbonate-substituted, calcium-deficient hydroxyapatite phase composition. As another example, the coating can be an osteoconductive mineral coating.

As another example, the mineral coating can include an apatite. Apatite can include calcium phosphate, calcium carbonate, calcium fluoride, calcium hydroxide, or citrate.

As another example, a mineral coating can comprise a plurality of discrete mineral islands on the scaffold, or the mineral coating can be formed on the entire surface of the scaffold. As another example, the mineral coating can comprise a substantially homogeneous mineral coating. In other embodiments, the mineral coatings can be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, anorganic bone or a mixture thereof. For example, an osteoconductive mineral coating can be calcium-deficient carbonate-containing hydroxyapatite.

As another example, the mineral coating can include hydroxyapatite. Calcium-deficient (non-stoichiometric) hydroxyapatite, $Ca_{10-x}(PO_4)_{6-x}(HPO_4)_x(OH)_{2-x}$ (where x is between 0 and 1) has a Ca/P ratio between 1.67 and 1.5. The Ca/P ratio is often used in the discussion of calcium phosphate phases. Stoichiometric apatite $Ca_{10}(PO_4)_6(OH)_2$ has a Ca/P ratio of 10:6 normally expressed as 1.67. The non-stoichiometric phases have the hydroxyapatite structure with cation vacancies ($Ca^{2+}$) and anion ($OH^-$) vacancies. Hydroxyapatite can be predominantly crystalline, but, in some cases, may be present in amorphous forms. The mineral coatings useful in this application can include from at least about 1% to at least about 100% hydroxyapatite, including the discrete values included in this range.

It is well known that the hydroxyapatite within the bones of living organisms are very thin plate-like carbonate structures which have an average of 50 nm length, 2-3 nm thickness and a width of 25 nm. (*Heliyon*, Volume 6, Issue 4, 2020, Article e03655)

In some embodiments, the mineral coating can include octacalcium phosphate. Octacalcium phosphate has a chemical formula of $Ca_8H_2(PO_4)_6 \cdot 5H_2O$ or can also be written as $Ca_4HO_{12}P_3$. Octacalcium phosphate has been shown to be a precursor of hydroxyapatite. Hydrolysis of octacalcium phosphate can create hydroxyapatite. Octacalcium phosphate can be predominantly crystalline, but, in some cases, may be present in amorphous forms. The mineral coating, in some aspects, can include at least about 1% to at least about 100% octacalcium phosphate including the discrete values included in this range.

The mineral coating useful for coating the lyophilized porous macroparticles can include at least about 1% or at least about 100% porosity including all discrete values included in this range. The mineral coating can also include a pore diameter from about 1 nm to about 3500 nm including all discrete values included in this range. The mineral coating useful in this application can include a ratio of at least about 0.1 Ca/P to about 10 Ca/P including the discrete values included in this range.

In many embodiments, the mineral coating covering the plurality of lyophilized porous macroparticles comprises a plate-like nanostructure comprising nanoparticles having a size range from about 100 to about 200 nanometers. In some embodiments, the size range of the nanoparticles can be form about 10 to about 100 nanometers. In some embodiments, the mineral coating comprises a calcium-containing mineral, the calcium-containing mineral is at least one of apatite, hydroxyapatite, α-tricalcium phosphate, β-tricalcium phosphate, amorphous calcium phosphate, dicalcium phosphate, octacalcium phosphate, calcium carbonate, a carbonated-substituted calcium-deficient hydroxyapatite, anorganic bone or combinations thereof. As used herein anorganic bone refers to bone mineral only, with the organic constituents removed. In other embodiments, the plurality of lyophilized porous macroparticles comprise tricalcium phosphate and hydroxyapatite.

The collagen can be from skin, tendon, fascia, ligament, trachea, or organ collagen. In certain embodiments, the collagen is human collagen or another mammalian collagen (e.g., porcine, bovine, or ovine). The collagen can be sourced from any animal.

Generally, there are about twenty-eight distinct collagen types that have been identified in vertebrates, including bovine, ovine, porcine, chicken, marine, and human sources. The collagen types are numbered by Roman numerals, and the chains found in each collagen type are identified by Arabic numerals. Detailed descriptions of structure and biological functions of the various types of naturally occurring collagens are generally available in the art.

The collagen may have the same composition as in naturally occurring sources. Examples of sources of collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen may further or alternatively comprise hetero- and homo-trimers of any of the above-recited collagen types. In some embodiments, the collagen comprises hetero- or homo-trimers of human collagen type I, human collagen type II, human collagen type III, or combinations thereof. In some embodiments, the collagen is type I or substantially all is collagen type I, e.g., at least 60%, at least 65%, at least 70%, at least 75%, at least 80%, at least 85%, at least 90%, or at least 95%.

Although the invention has been described with reference to preferred embodiments, persons skilled in the art will recognize that changes may be made in form and detail without departing from the spirit and scope of the invention.

What is claimed is:

1. A system for making a coated bone material under a sterilized environment, the system comprising a container comprising an opening configured for adding bone material to be coated to the container, a seal configured to enclose the bone material in the interior of the container, an inlet configured to add a coating liquid to the interior of the container, an outlet, separate from the inlet, and configured to remove any excess coating liquid from the interior of the container, and a sensor configured to detect a parameter within the interior of the container; a reactor configured to receive and hold the container, the reactor having a balance configured to move and tilt at least one end of the container to mix the coating liquid with the bone material, and the reactor having a heating element, wherein the outlet is configured to remove excess coating material when the coating liquid is coating the bone material.

2. The system of claim 1, further comprising a heating element configured for controlling the temperature of the interior of the container.

3. The system of claim 1, wherein the container is in the form of a flexible bag.

4. The system of claim 1, wherein the outlet comprises a gas output configured to adjust a pressure in the container.

* * * * *